(12) United States Patent
Balesh et al.

(10) Patent No.: US 12,728,242 B2
(45) Date of Patent: Sep. 8, 2026

(54) SYSTEMS AND METHODS FOR PERCUTANEOUS DRAINAGE

(71) Applicant: NoviRad, Inc., Houston, TX (US)

(72) Inventors: Elie Rashid Balesh, El Paso, TX (US); Matthew Isaac Pena, Houston, TX (US); Linh Quoc Vu, Manvel, TX (US); Roi Jeric Garcia Bautista, Houston, TX (US)

(73) Assignee: NoviRad, Inc., Houston, TX (US)

( * ) Notice: Subject to any disclaimer, the term of this patent is extended or adjusted under 35 U.S.C. 154(b) by 336 days.

(21) Appl. No.: 17/574,497

(22) Filed: Jan. 12, 2022

(65) Prior Publication Data

US 2022/0218962 A1 Jul. 14, 2022

Related U.S. Application Data

(60) Provisional application No. 63/137,092, filed on Jan. 13, 2021.

(51) Int. Cl.
*A61M 27/00* (2006.01)
*A61M 1/00* (2006.01)

(52) U.S. Cl.
CPC ............ *A61M 27/00* (2013.01); *A61M 1/912* (2021.05); *A61M 1/915* (2021.05); *A61M 1/96* (2021.05); *A61M 1/98* (2021.05)

(58) Field of Classification Search
CPC ...... A61M 27/00; A61M 1/915; A61M 1/912; A61M 1/96; A61M 1/98
See application file for complete search history.

(56) References Cited

U.S. PATENT DOCUMENTS 5,002,528 A * 3/1991 Palestrant ............... A61M 1/70 604/246
6,012,181 A * 1/2000 Johnson .................. A61F 5/445 604/323

(Continued)

FOREIGN PATENT DOCUMENTS

WO WO 94/17849 A1 8/1994
WO WO 2020/146454 A1 7/2020

OTHER PUBLICATIONS

International Search Report and Written Opinion of the International Searching Authority, mailed Apr. 1, 2022, for International Application No. PCT/US2022/012188.

(Continued)

*Primary Examiner* — Rebecca E Eisenberg
*Assistant Examiner* — Kate Elizabeth Strachan
(74) *Attorney, Agent, or Firm* — Baker Botts L.L.P.

(57) ABSTRACT

System for percutaneous drainage of a drainage site includes a catheter, a drain tube, a first pump, a flush tube, a second pump, and a controller. The catheter includes a drain lumen defined by a first portion of a catheter wall and a septum, and a flush lumen defined by a second portion of the catheter wall and the septum. The flush lumen is separated from the drain lumen by the septum. The septum has at least one septal hole disposed therein such that the drain lumen and the flush lumen are in communication via the at least one septal hole. The catheter wall has at least one wall hole disposed therein such that the drain lumen is in communication with the drainage site when the distal end portion of the catheter is placed within the drainage site.

31 Claims, 23 Drawing Sheets
(8 of 23 Drawing Sheet(s) Filed in Color)

(56) References Cited

U.S. PATENT DOCUMENTS

| | | | | |
|---|---|---|---|---|
| 7,674,237 | B2 | 3/2010 | O'Mahony et al. | |
| 9,199,014 | B2 * | 12/2015 | Hall | A61M 3/0208 |
| 10,485,568 | B2 | 11/2019 | Donnelly et al. | |
| 10,492,805 | B2 | 12/2019 | Culbert et al. | |
| 10,702,292 | B2 | 7/2020 | Look et al. | |
| 10,716,880 | B2 | 7/2020 | Culbert et al. | |
| 2005/0033264 | A1 | 2/2005 | Redinger | |
| 2009/0054855 | A1 * | 2/2009 | Blott | A61M 35/30 604/290 |
| 2009/0157002 | A1 * | 6/2009 | Dumot | A61M 25/007 604/523 |
| 2009/0192435 | A1 * | 7/2009 | Gregersen | A61M 25/007 604/28 |
| 2010/0069886 | A1 | 3/2010 | Wilkes | |
| 2012/0123323 | A1 * | 5/2012 | Kagan | A61M 1/743 604/35 |
| 2014/0163530 | A1 | 6/2014 | Frenkel | |
| 2015/0165172 | A1 * | 6/2015 | Wall, II | A61F 13/05 604/541 |
| 2020/0139024 | A1 * | 5/2020 | Pratt | A61M 1/73 |

OTHER PUBLICATIONS

Extended European Search Report dated Oct. 16, 2024 in Application No. EP 22740008.

* cited by examiner

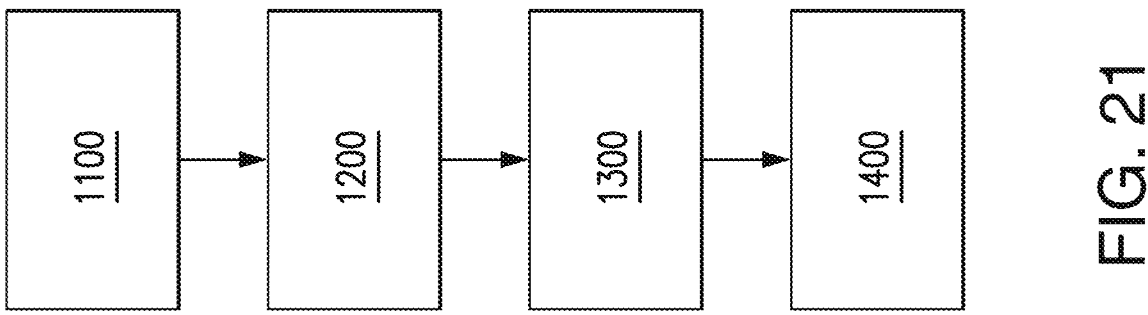
FIG. 21
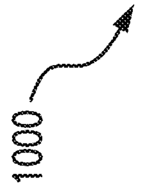

SYSTEMS AND METHODS FOR PERCUTANEOUS DRAINAGE

FIELD OF DISCLOSED SUBJECT MATTER

The disclosed subject matter is directed to systems and methods for percutaneous drainage, for example, for the evacuation of abnormal, possibly infected, fluid collections from the body.

DESCRIPTION OF RELATED ART

Pathologic fluid can build up in a body due to infection/inflammation (i.e., an abscess), visceral obstruction/perforation (i.e., blockages of the urinary or biliary tracts), and/or hemorrhage (i.e., a hematoma). The fluid can be drained using an image-guided percutaneous drainage system. For example, using computed tomographic (CT), sonographic (US), and/or fluoroscopic (XR) guidance, medical practitioners (e.g., interventional radiologists) can non-invasively visualize abnormal fluid collections and subsequently insert drainage catheters into the collections through the skin using minimally invasive techniques.

Drainage catheters can be hollow plastic tubes of variable length and luminal diameter, with the most commonly used type known as a “pigtail” catheter in reference to the looped shape that its distal end forms. Drainage catheters function via the presence of one or more side holes at their distal end, through which abnormal fluid can enter the lumen of the catheter and be collected into a bag attached to its proximal end. Drainage can occur under the force of gravity or intermittently applied bulb suction. The average dwell time for a drainage catheter can be about 28 days, and device failure secondary to luminal obstruction/occlusion by viscous fluid and/or particulate matter can occur about 25-30% of the time, regardless of tube diameter. Faulty drainage can result in the recrudescence of patient illness and can require repeat invasive procedures, which can include additional risks and costs, to prevent sepsis-related death. Research has shown that up to 85% of drainage catheters can require exchange at least once before removal, and 50% can undergo upsizing, even though larger diameters have been shown not to confer a significant advantage in luminal patency or required dwell time.

To help maintain luminal patency, healthcare providers, as well as patients and/or caregivers, can be instructed to manually inject a defined volume of sterile saline into the catheter at scheduled frequencies. This can increase luminal lubricity, dislodge adherent debris from the catheter walls and side holes, and reduce the viscosity of draining fluid. However, this intervention is not always effective, and non-compliance with instructions is a common problem. Forgetting to flush catheters, injecting too little or too much fluid, and substitution of non-sterile tap water for sterile saline are common reasons for catheter occlusion, delayed healing, and additional complications, such as catheter-associated superficial or deep tissue infections.

Furthermore, patients commonly report the negative psychosocial effects of living with one or more drainage catheters for prolonged periods of time. The tubes and waste collection bags can be physically cumbersome, uncomfortable, unsightly, and socially stigmatizing.

Accordingly, there is a need for improved systems and methods for percutaneous drainage.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended figures.

To achieve these and other advantages and in accordance with the purpose of the disclosed subject matter, as embodied and broadly described, the disclosed subject matter is directed to systems and methods for percutaneous drainage. For example, a system for percutaneous drainage of a drainage site includes a catheter, a drain tube, a first pump, a flush tube, a second pump, and a controller. The catheter includes a catheter wall extending from a proximal end portion of the catheter to a distal end portion of the catheter, the distal end portion of the catheter configured for placement within the drainage site, a septum disposed within the catheter wall and extending from a proximal end portion of the catheter to a distal end portion of the catheter, a drain lumen defined by a first portion of the catheter wall and the septum, the drain lumen extending from the proximal end portion of the catheter to the distal end portion of the catheter, and a flush lumen defined by a second portion of the catheter wall and the septum, the flush lumen extending from the proximal end portion of the catheter to the distal end portion of the catheter, wherein the flush lumen is separated from the drain lumen by the septum. The drain tube has a first end portion coupled to the drain lumen at the proximal end portion of the catheter, and a second end portion coupled to a waste collection container. The first pump is coupled to the drain tube between the first end portion of the drain tube and the second end portion of the drain tube. The flush tube includes a first end portion coupled to the flush lumen at the proximal end portion of the catheter, and a second end portion coupled to a flush material container having a flush material disposed therein. The second pump is coupled to the flush tube between the first end portion of the flush tube and the second end portion of the flush tube. The controller is coupled to the first pump and the second pump for controlling the first pump and the second pump. The septum has at least one septal hole disposed therein proximate to the distal end portion of the catheter such that the drain lumen and the flush lumen are in communication via the at least one septal hole. The catheter wall has at least one wall hole disposed therein proximate to the distal end portion of the catheter such that the drain lumen is in communication with the drainage site when the distal end portion of the catheter is placed within the drainage site.

The volume of the drain lumen can be equal to a volume of the flush lumen. The volume of the drain lumen can be greater than the volume of the flush lumen. The at least one septal hole can include a plurality of septal holes. The at least one septal hole can include a distal hole having a first diameter and a proximal hole having a second diameter, the second diameter being different than the first diameter. The second diameter can be smaller than the first diameter. The at least one septal hole and the at least one wall hole can be offset.

The system can include a pressure sensor or flow monitoring sensors coupled to the drain tube and the controller. The system can include a housing having the first pump, the second pump, and the controller disposed therein. The system can include an injection port coupled to the flush tube. The system can include a syringe coupled to the injection port by a third tube and/or the system can include a third pump coupled to the injection port by a third tube.

In accordance with the disclosed subject matter, a catheter for percutaneous drainage of a drainage site is provided. The catheter can include a catheter wall extending from a proximal end portion of the catheter to a distal end portion of the catheter, the distal end portion of the catheter configured for placement within the drainage site; a septum disposed within the catheter wall and extending from a proximal end portion of the catheter to a distal end portion of the catheter; a drain lumen defined by a first portion of the catheter wall and the septum, and extending from the proximal end portion of the catheter to the distal end portion of the catheter; and a flush lumen defined by a second portion of the catheter wall and the septum, and extending from the proximal end portion of the catheter to the distal end portion of the catheter, wherein the flush lumen is separated from the drain lumen by the septum. The septum can have at least one septal hole disposed therein proximate to the distal end portion of the catheter such that the drain lumen and the flush lumen are in communication via the at least one septal hole. The catheter wall has at least one wall hole disposed therein proximate to the distal end portion of the catheter such that the drain lumen is in communication with the drainage site when the distal end portion is placed within the drainage site.

In accordance with the disclosed subject matter, a method of percutaneous drainage of a drainage site is provided. The method can include inserting a catheter into the drainage site, the catheter including a catheter wall extending from a proximal end portion of the catheter to a distal end portion of the catheter, the distal end portion of the catheter configured for placement within the drainage site; a septum disposed within the catheter wall and extending from a proximal end portion of the catheter to a distal end portion of the catheter; a drain lumen defined by a first portion of the catheter wall and the septum, and extending from the proximal end portion of the catheter to the distal end portion of the catheter; and a flush lumen defined by a second portion of the catheter wall and the septum, and extending from the proximal end portion of the catheter to the distal end portion of the catheter, wherein the flush lumen is separated from the drain lumen by the septum; wherein the septum has at least one septal hole disposed therein proximate to the distal end portion of the catheter such that the drain lumen and the flush lumen are in communication via the at least one septal hole; and wherein the catheter wall has at least one wall hole disposed therein proximate to the distal end portion of the catheter such that the drain lumen is in communication with the drainage site when the distal end portion is placed within the drainage site. The method can further include withdrawing fluid from the drainage site via the drain lumen; identifying an occlusion in the drain lumen; and flushing a flush fluid through the flush lumen and into the drain lumen via the at least one septal hole and thereby removing the occlusion; and resuming withdrawing fluid from the drainage site via the drain lumen.

The method can include pausing withdrawing fluid from the drainage site via the drain lumen. Pausing can include reversing a direction of fluid flow in the drain lumen. The method can include monitoring a rate of fluid withdrawal from the drainage site. The method can include resuming withdrawing fluid from the drainage site via the drain lumen. The method can include monitoring a rate of change of the rate of fluid withdrawal from the drainage site. Identifying an occlusion in the drain can be based at least in part on one or more of the rate of fluid withdrawal from the drainage site and the rate of change of the rate of fluid withdrawal from the drainage site. The method can include monitoring a pressure in the waste lumen. The method can include monitoring a rate of change of the pressure in the waste lumen. Identifying an occlusion in the drain lumen can be based at least in part on one or more of the pressure in the waste lumen and a rate of change of the pressure in the waste lumen.

In accordance with the disclosed subject matter, a system for percutaneous drainage of a drainage site can include a catheter, a drain tube, a first pump, a flush tube, a second pump, and a controller. The catheter includes a catheter wall extending from a proximal end portion of the catheter to a distal end portion of the catheter, the distal end portion of the catheter configured for placement within the drainage site, a septum disposed within the catheter wall and extending from a proximal end portion of the catheter to a distal end portion of the catheter, a drain lumen defined by a first portion of the catheter wall and the septum, and extending from the proximal end portion of the catheter to the distal end portion of the catheter, and a flush lumen defined by a second portion of the catheter wall and the septum, and extending from the proximal end portion of the catheter to the distal end portion of the catheter, wherein the flush lumen is separated from the drain lumen by the septum. The drain tube has a drain tube having a first end portion coupled to the drain lumen at the proximal end portion of the catheter, and a second end portion coupled to a waste collection container. The first pump is coupled to the drain tube between the first end portion of the drain tube and the second end portion of the drain tube. The flush tube includes a first end portion coupled to the flush lumen at the proximal end portion of the catheter, and a second end portion coupled to a flush material container having a flush material disposed therein. The second pump is coupled to the flush tube between the first end portion of the flush tube and the second end portion of the flush tube. The controller is coupled to the first pump and the second pump for controlling the first pump and the second pump. The first portion of the catheter wall has at least a first wall hole disposed therein proximate to the distal end portion of the catheter such that the drain lumen is in communication with the drainage site when the distal end portion of the catheter is placed within the drainage site. The second portion of the catheter wall has at least a second wall hole disposed therein proximate to the distal end portion of the catheter such that the flush lumen is in communication with the drainage site when the distal end portion of the catheter is placed within the drainage site.

DRAWINGS

The patent or application file contains at least one drawing executed in color. Copies of this patent or patent application publication with color drawing(s) will be provided by the Office upon request and payment of the necessary fee.

Figure 1A:
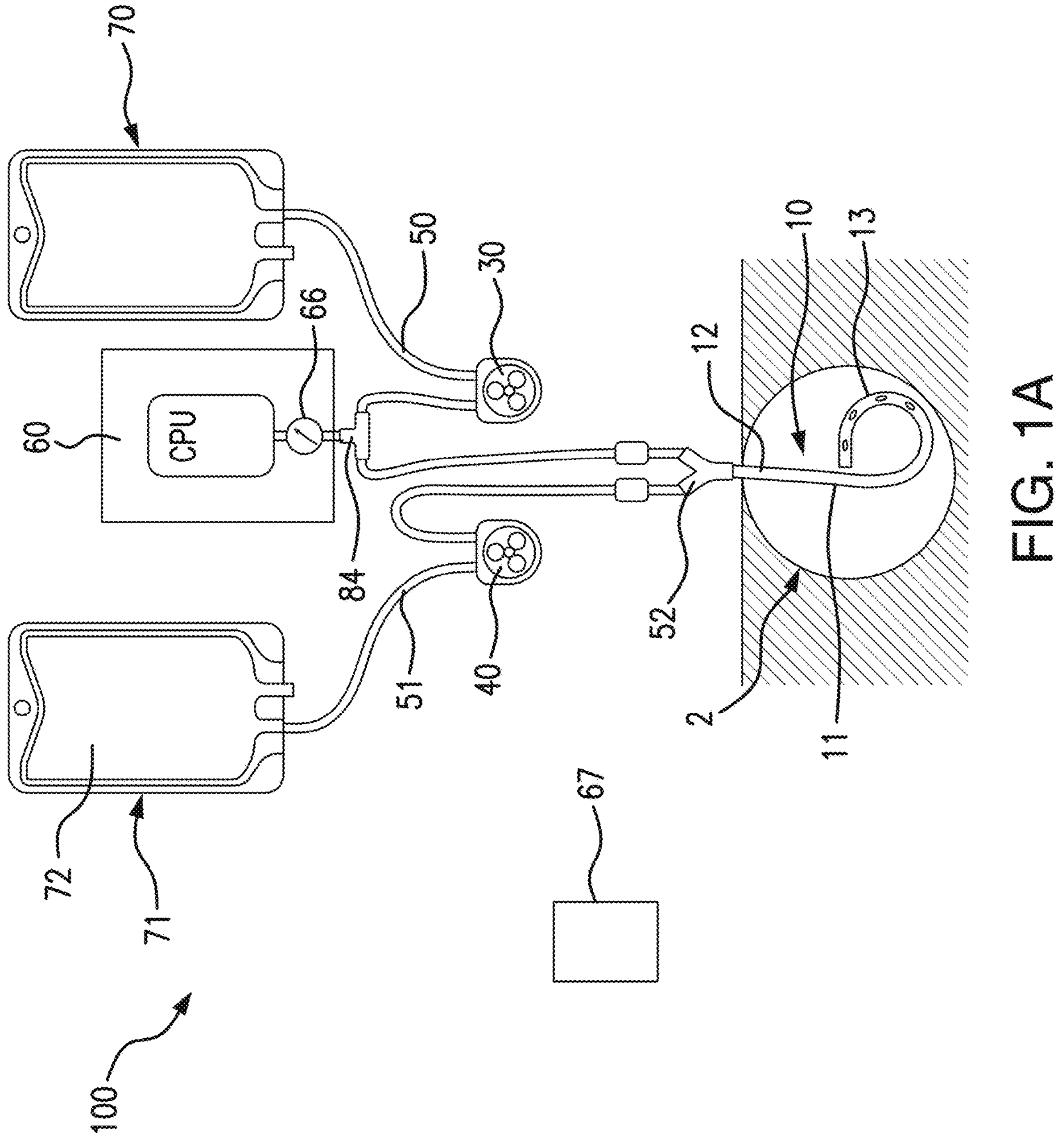
FIG. 1A is a schematic of an exemplary system for percutaneous drainage in accordance with the disclosed subject matter.
Figure 3C:
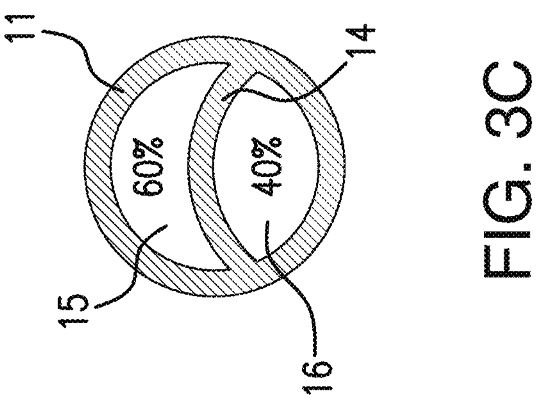
Figure 3B:
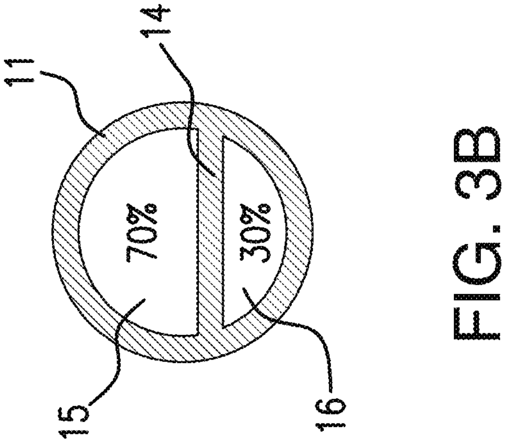
Figure 3A:
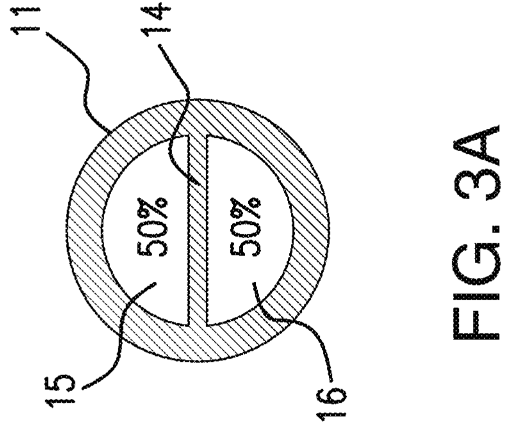

FIGS. 3A-3C provide cross-section views of exemplary catheters for use with the system of FIG. 1A, in accordance with the disclosed subject matter.

Figure 4:
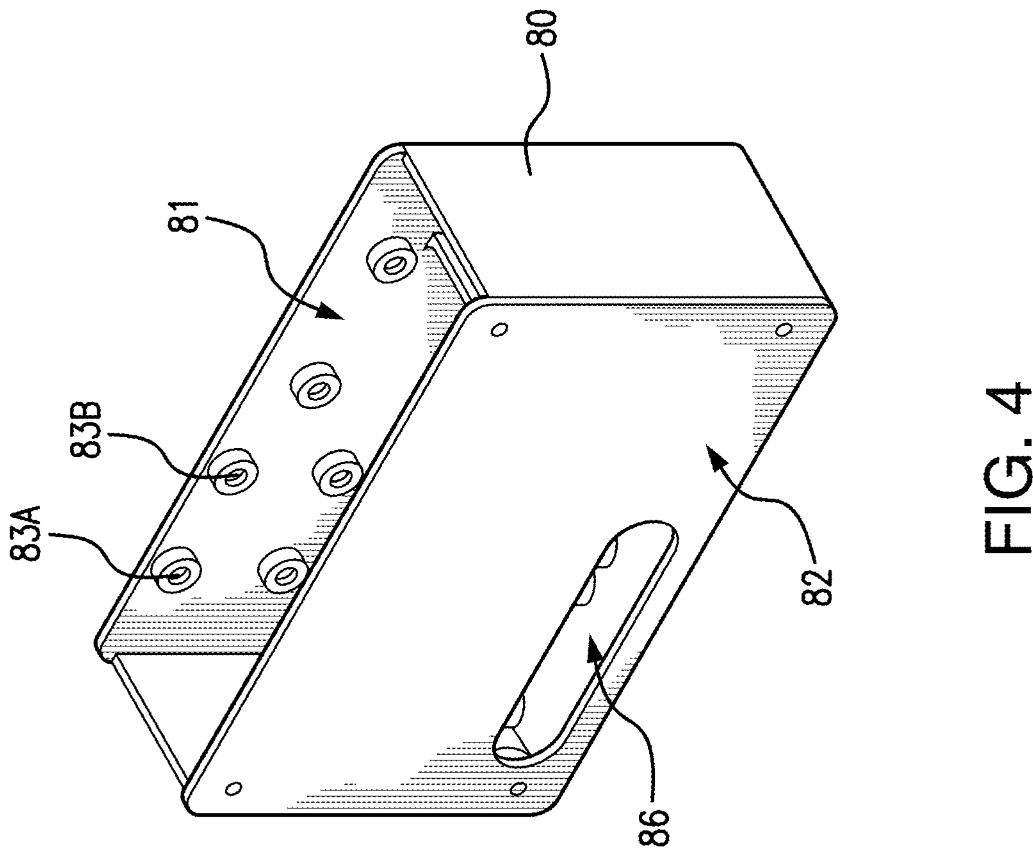

FIG. 4 is a perspective view of an exemplary housing for use with the system of FIG. 1A, in accordance with the disclosed subject matter.

Figures 5A, 5B:
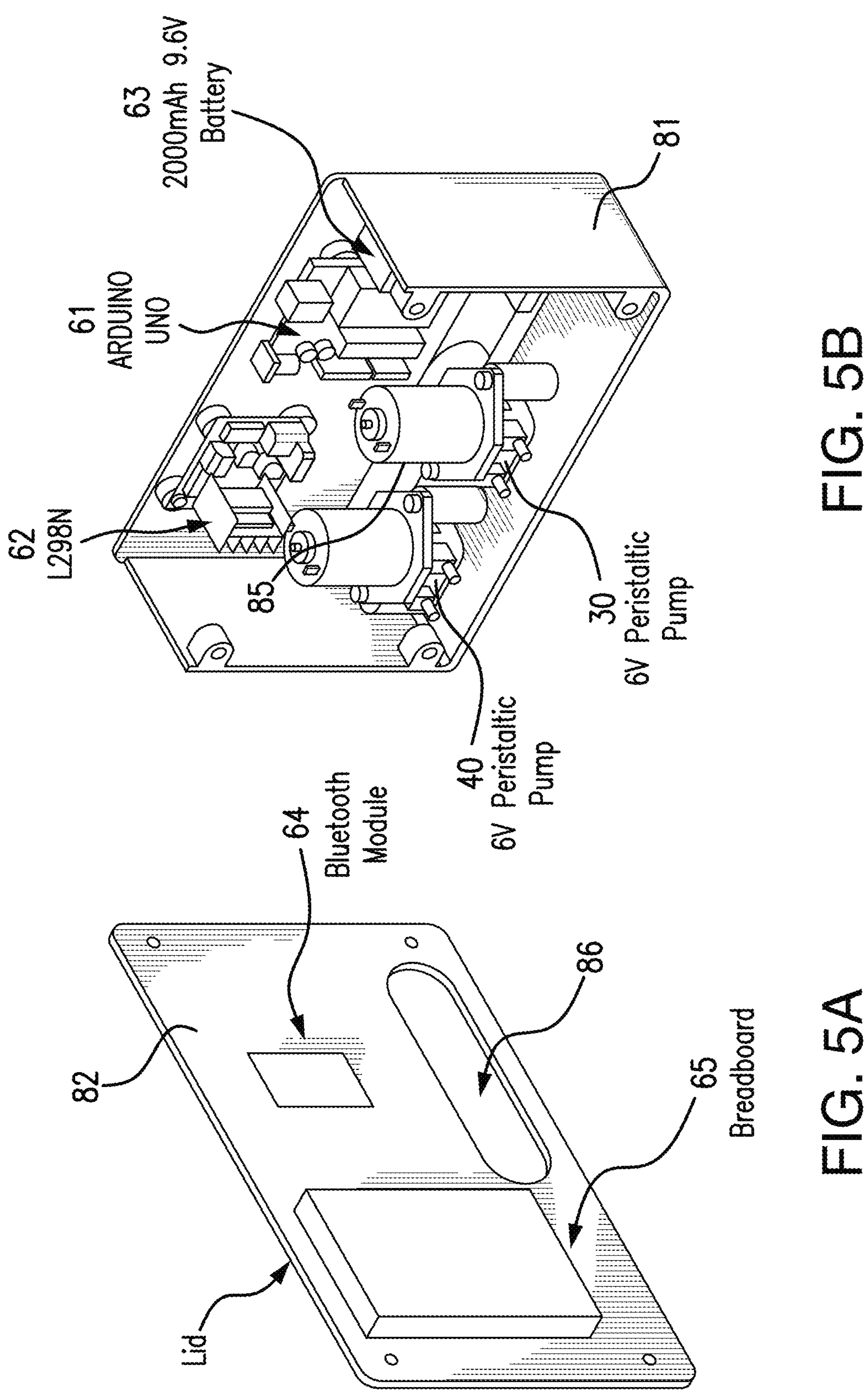

FIGS. 5A and 5B are perspective views of an exemplary base and cover, respectively, along with certain elements for use with the system of FIG. 1A, in accordance with the disclosed subject matter.

Figure 6:
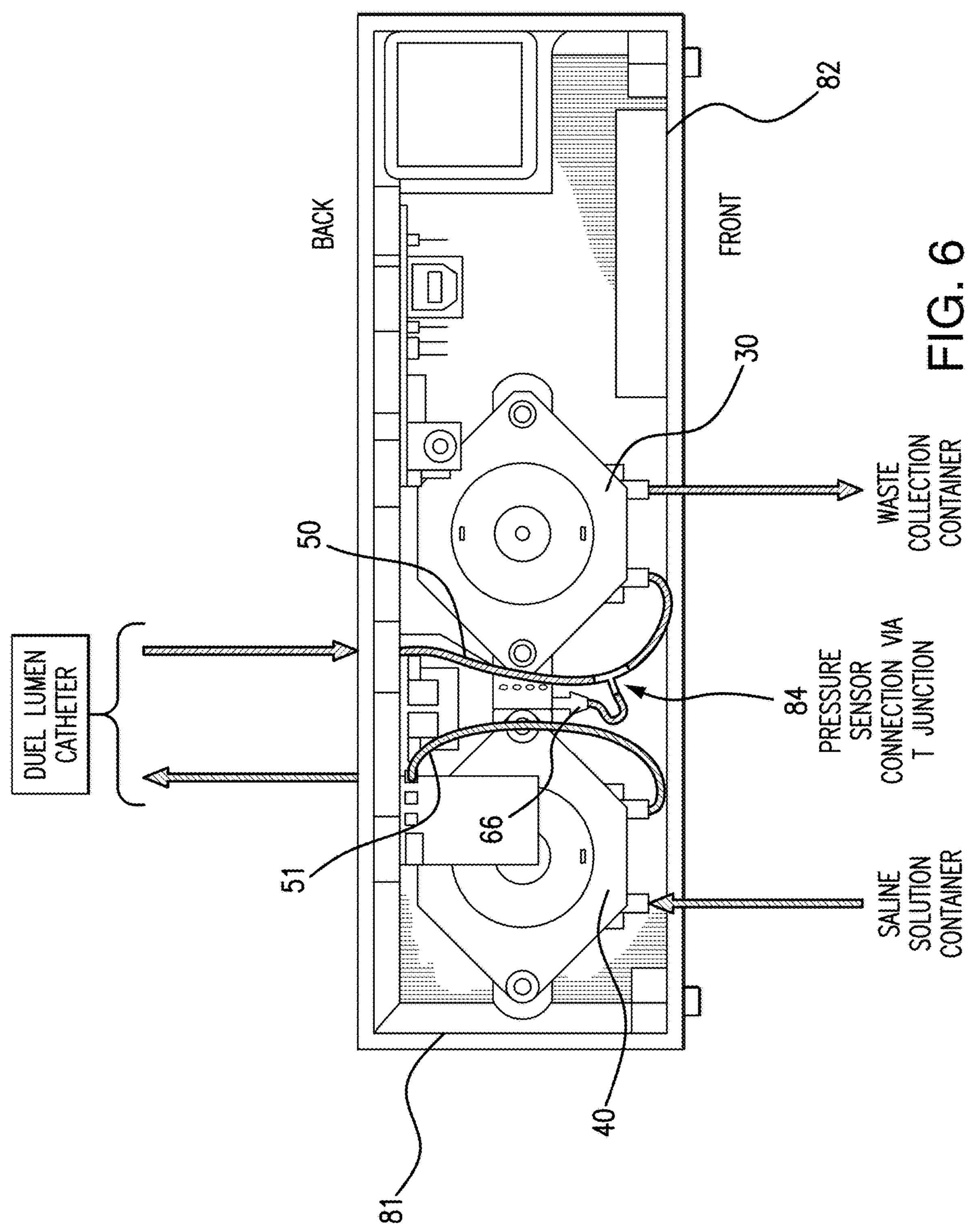

FIG. 6 is a top-down, cut-away view of an exemplary housing, along with certain elements for use with the system of FIG. 1A, in accordance with the disclosed subject matter.

Figure 7:
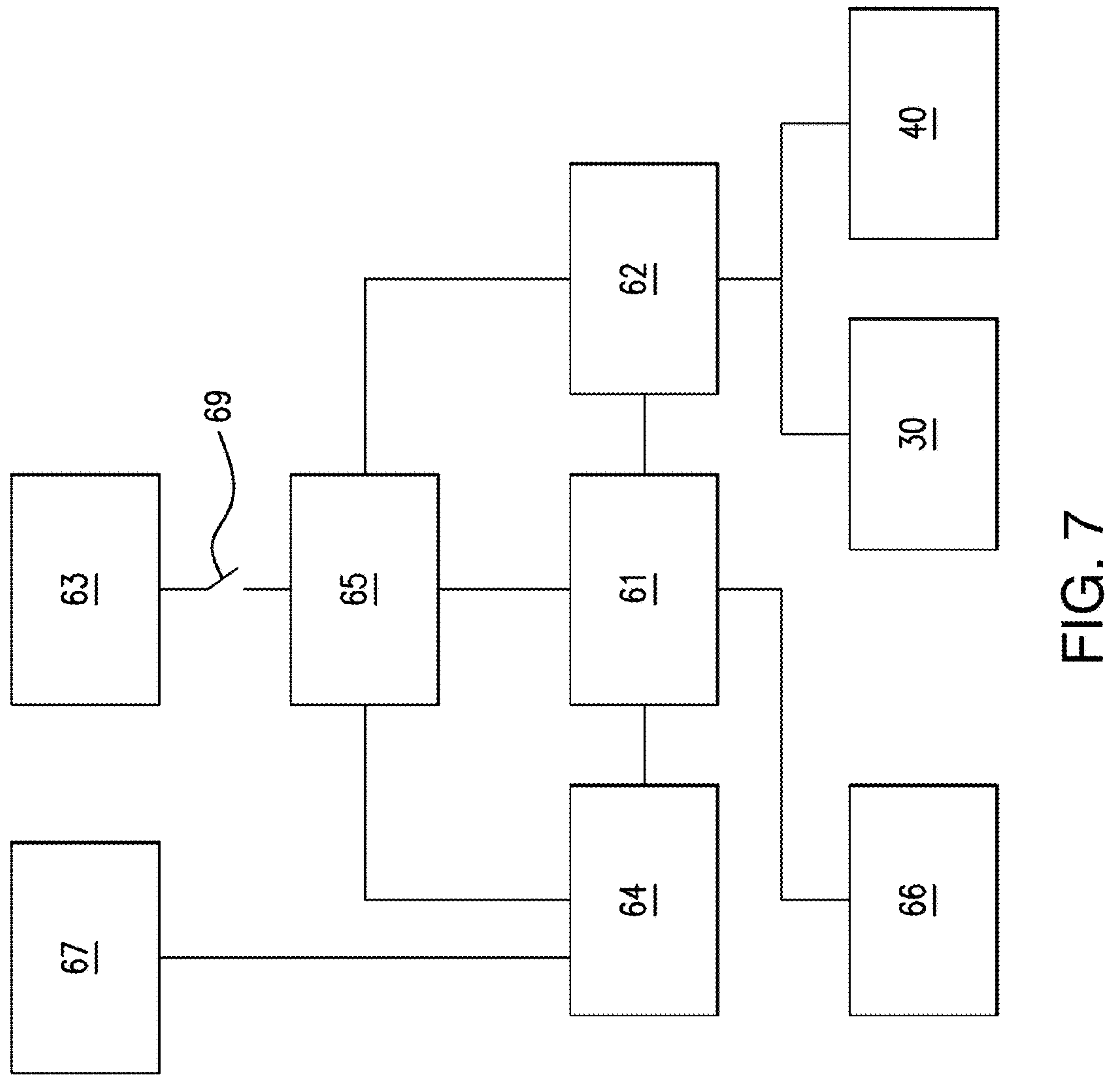

FIG. 7 is a block diagram of certain elements for use with the system of FIG. 1A, in accordance with the disclosed subject matter.

Figure 8:
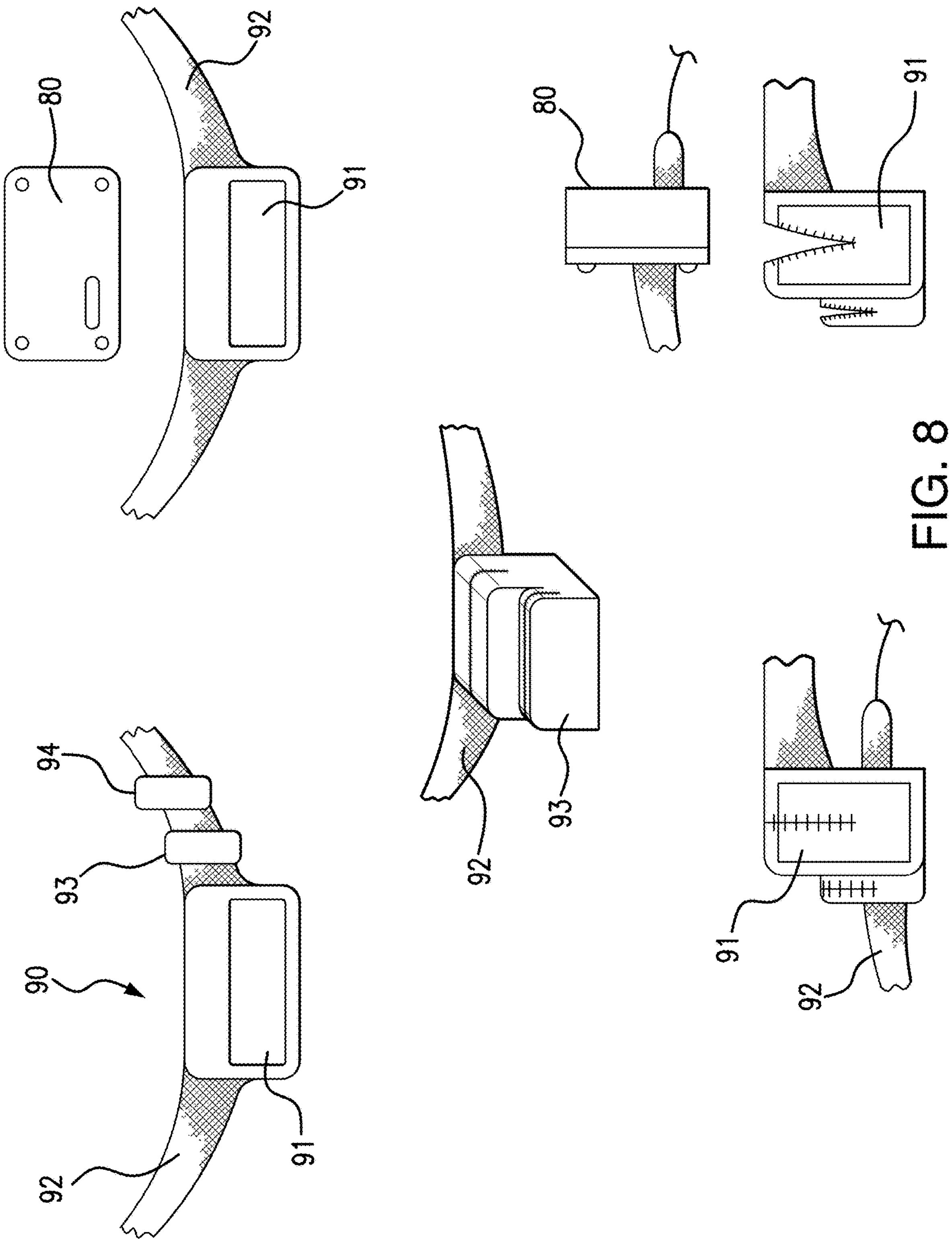

FIG. 8 provides a plurality of views of a wearable component for use with the system of FIG. 1A, in accordance with the disclosed subject matter.

Figures 9A, 9B, 9C:
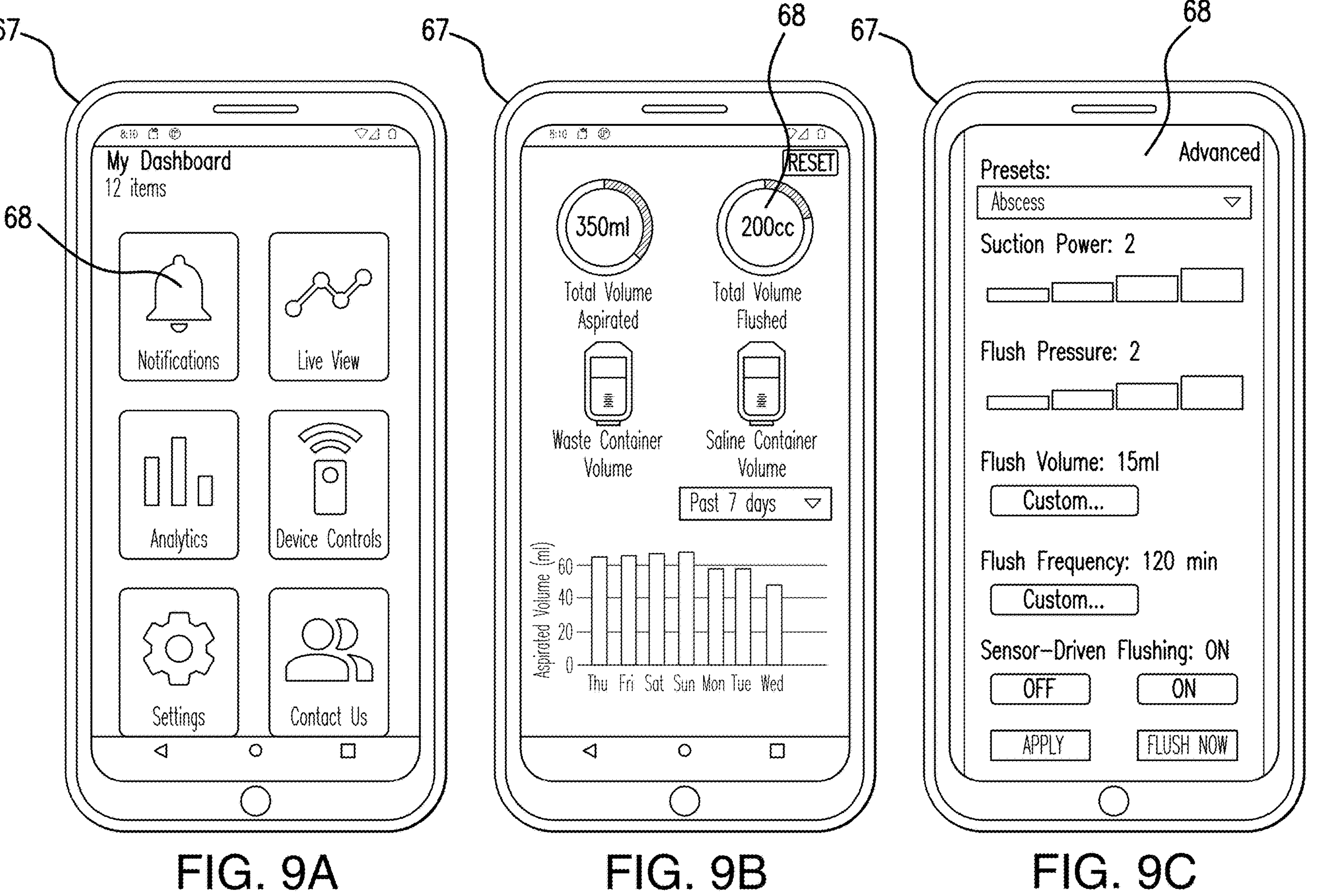

FIGS. 9A-9C provide views of a graphical user interface for use with the system of FIG. 1A.

Figure 10:
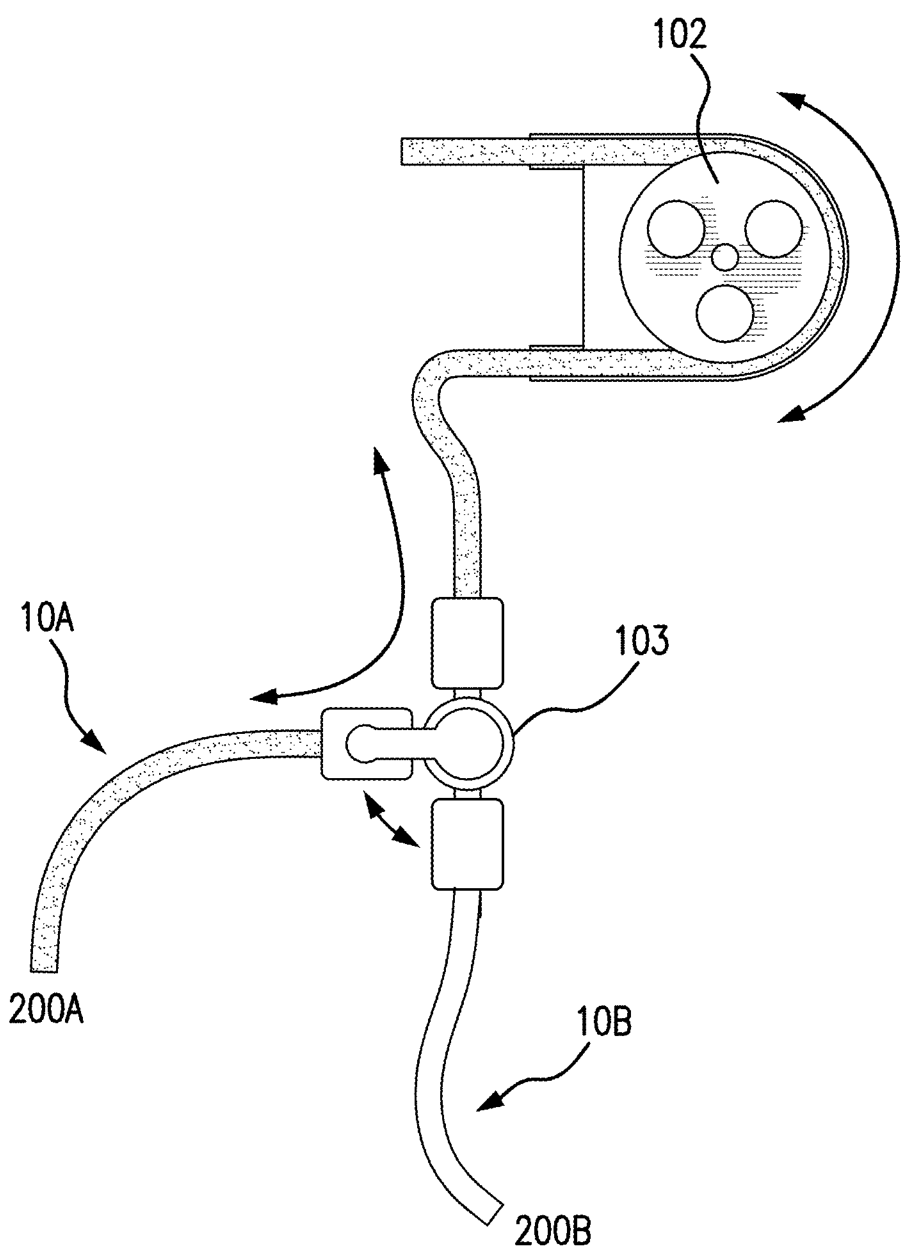

FIG. 10 is a schematic of a portion of an exemplary system for percutaneous drainage including multiple drainage catheters, in accordance with the disclosed subject matter.

Figure 11:
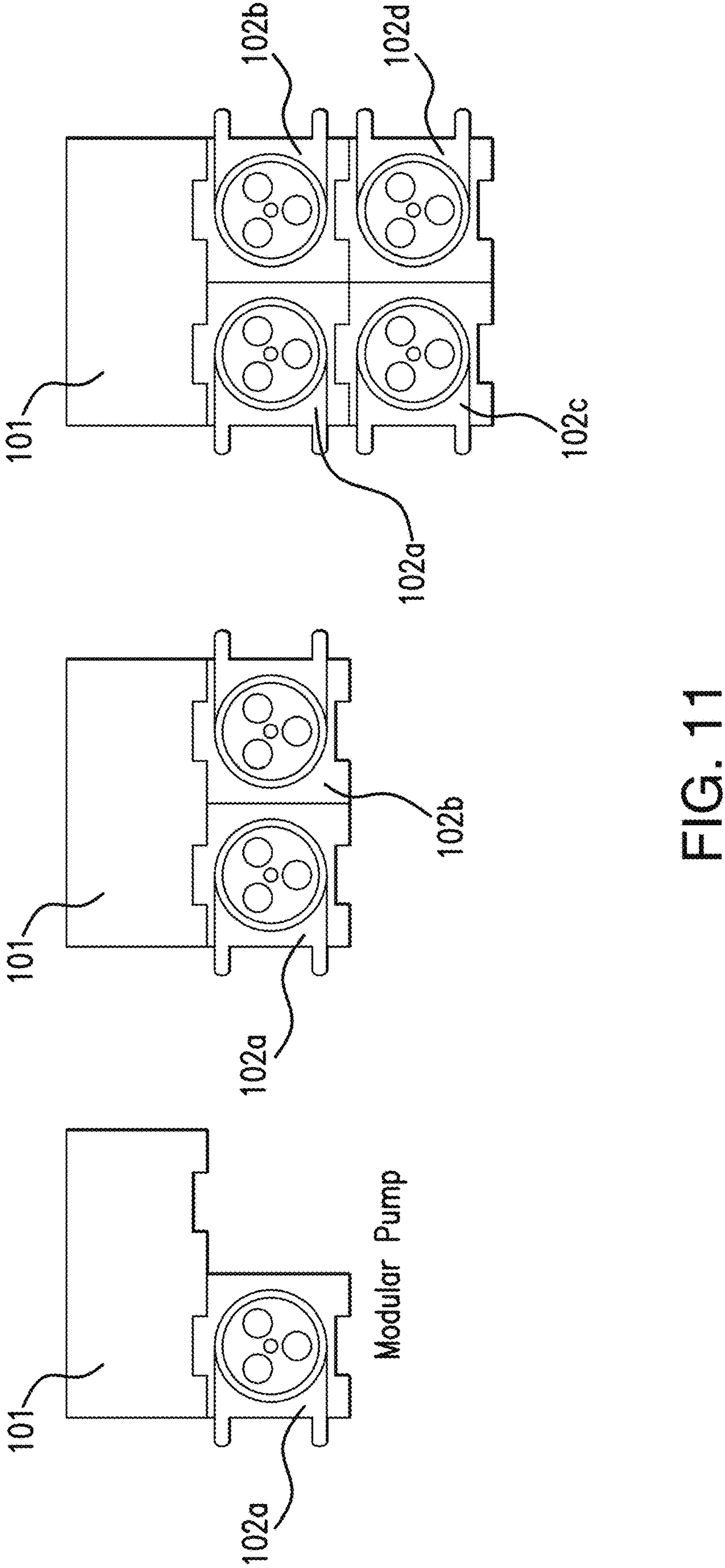

FIG. 11 illustrates a control unit coupled to one or more modular pumps, in accordance with the disclosed subject matter.

Figure 12:
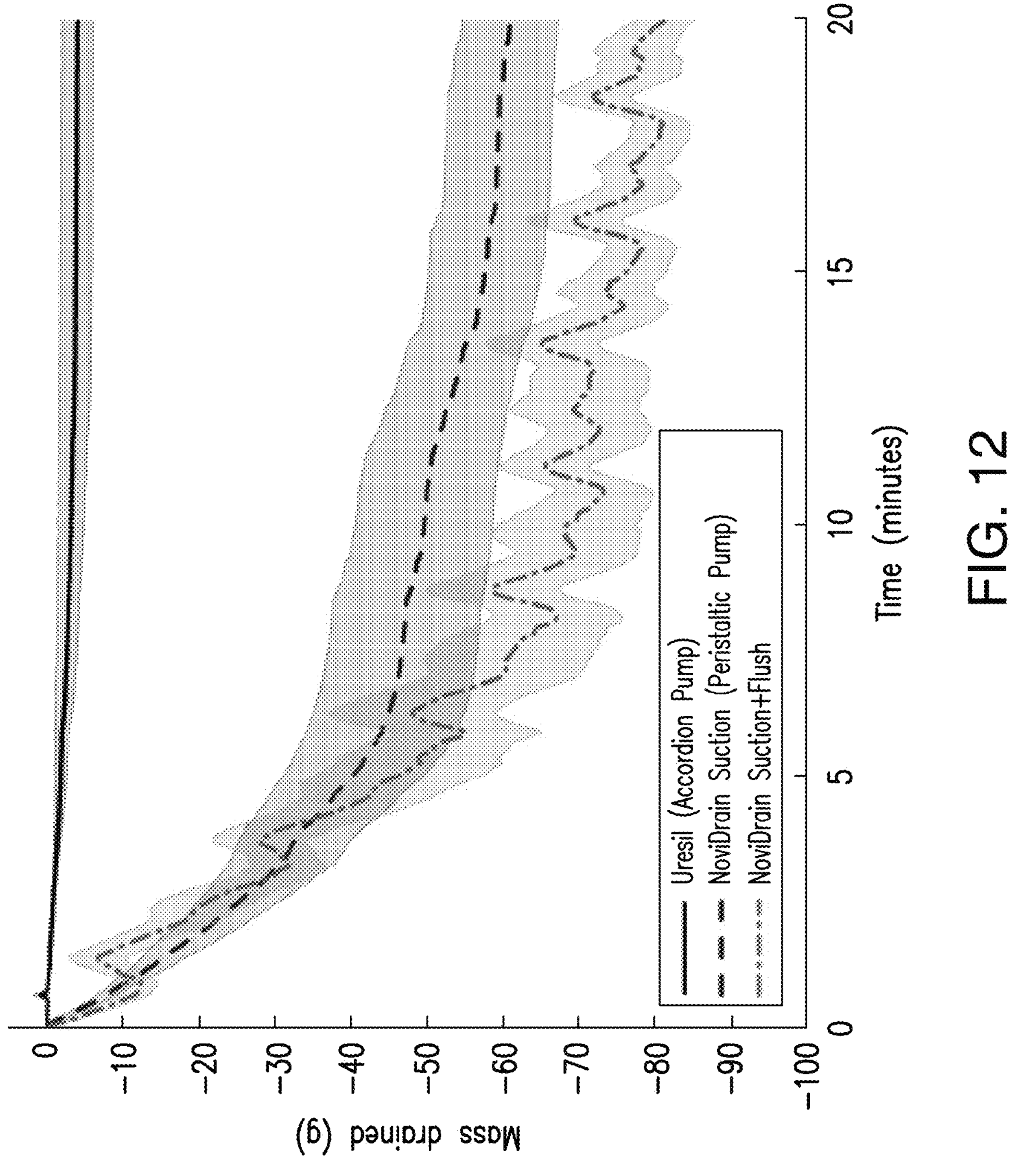
Figure 13:
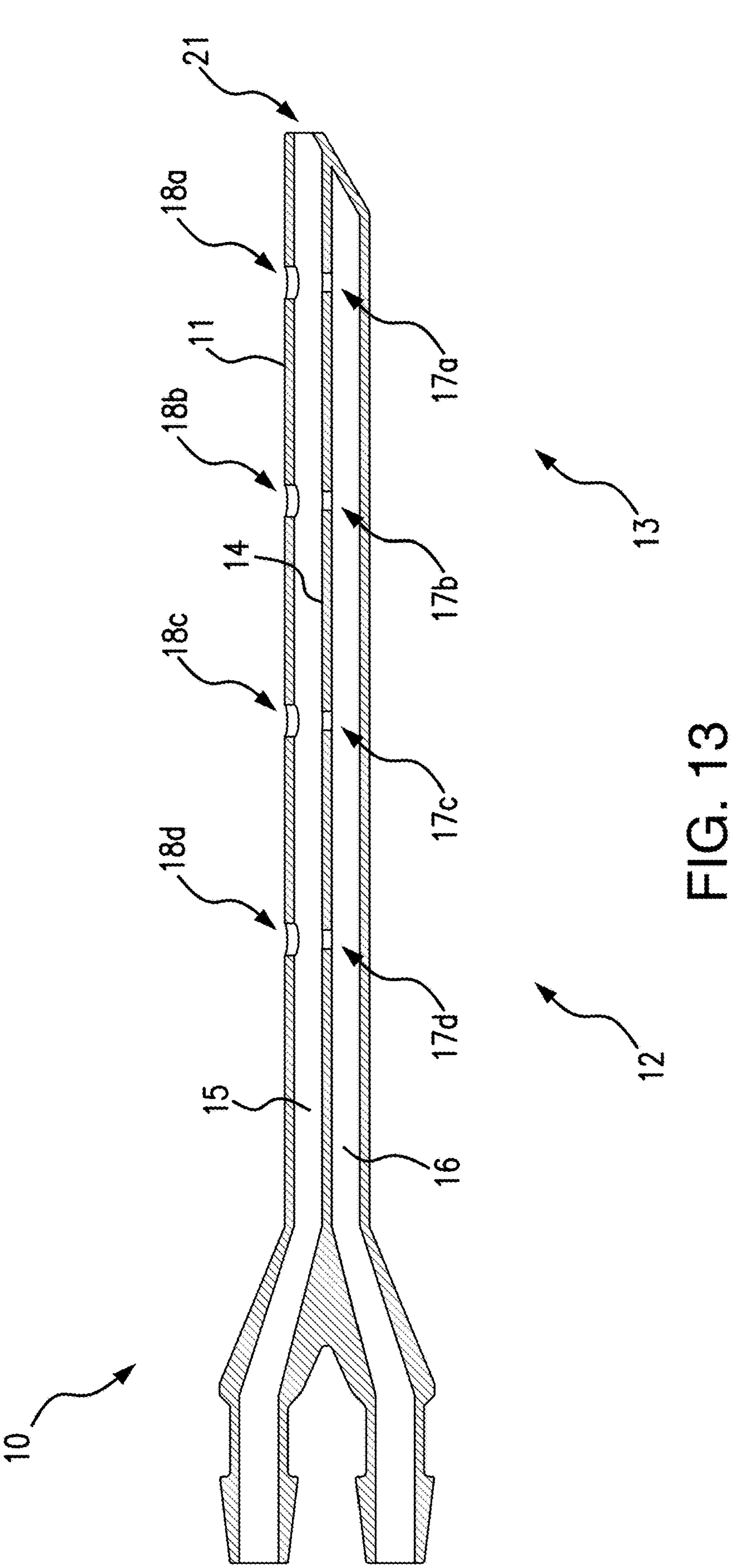
Figure 14:
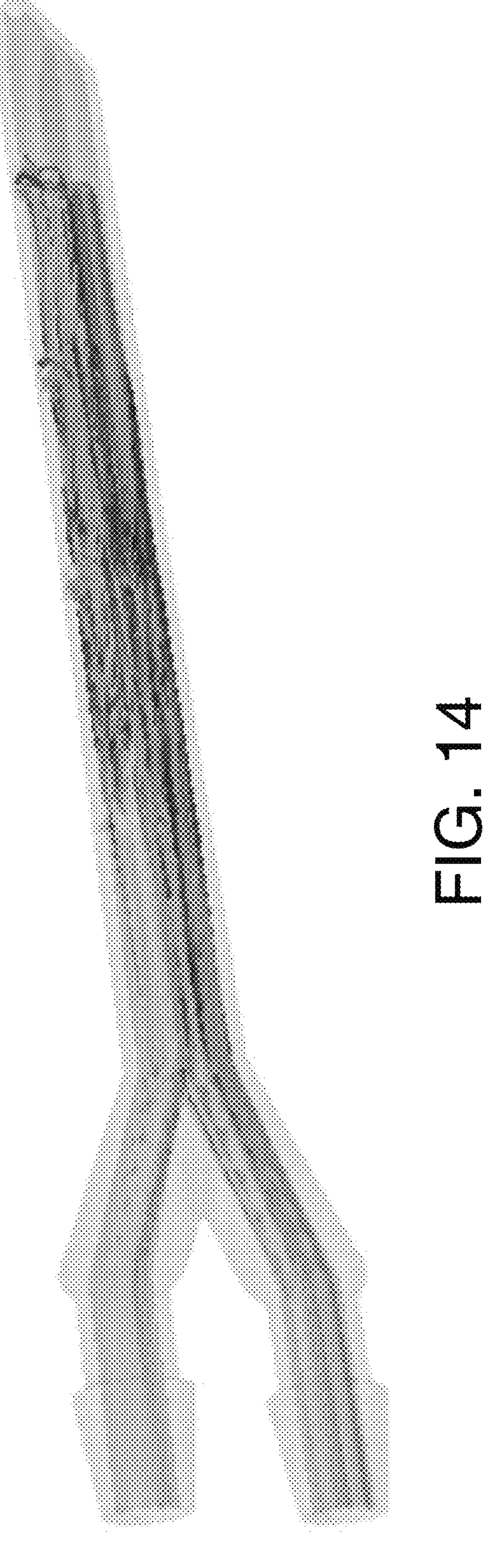

FIG. 12 is a plot of the results of suction over 20 minutes through a draining catheter in accordance with the disclosed subject matter using the three different suction conditions is shown FIG. 13 is a schematic of an exemplary catheter in accordance with the disclosed subject matter used for computational fluid dynamics analysis, FIG. 14 illustrates exemplary results of computational fluid dynamics analysis of a catheter, in accordance with disclosed subject matter.

Figure 15:
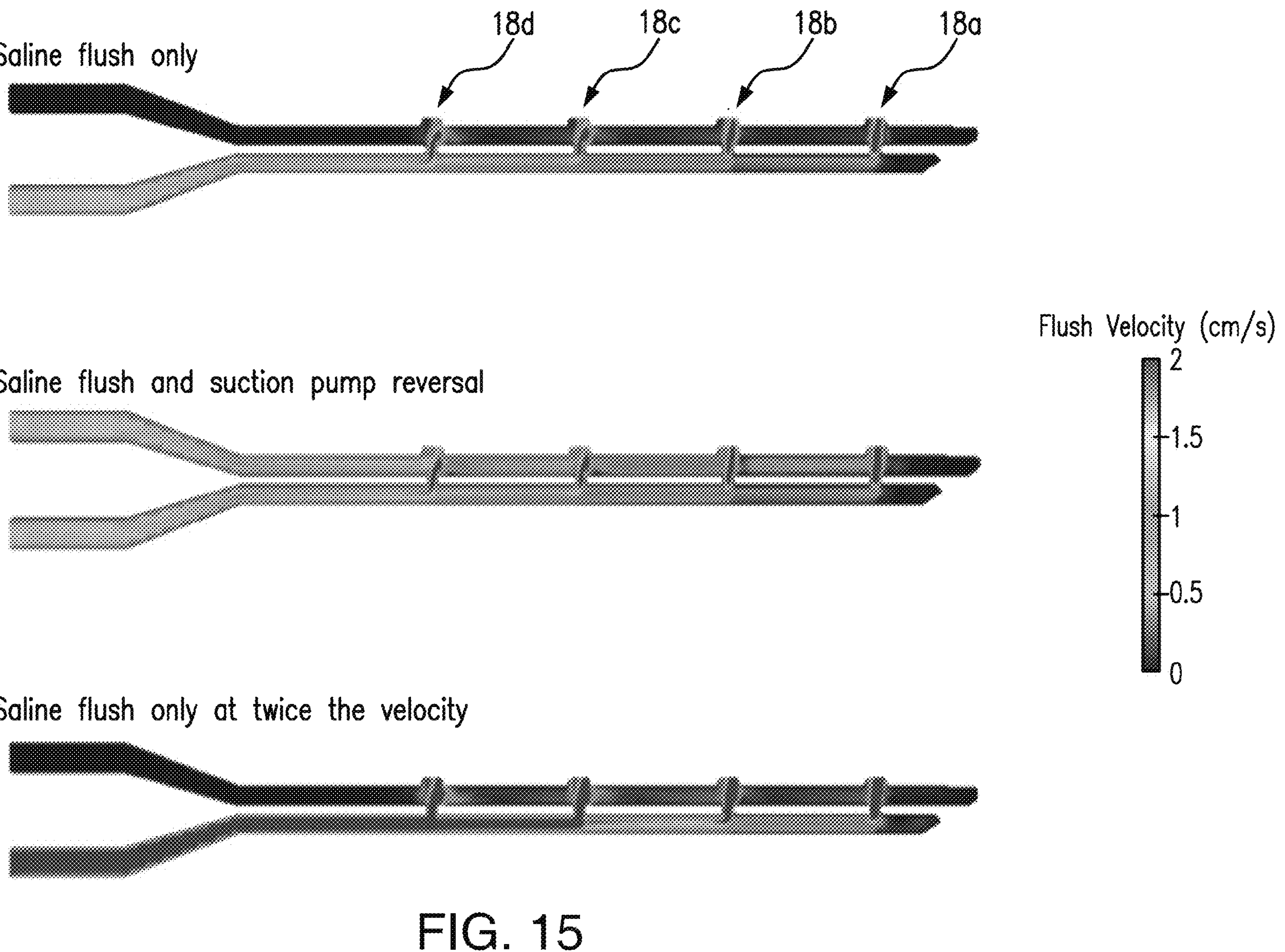

FIG. 15 illustrates exemplary results of computational fluid dynamics analysis catheters employing varying flush strategies, in accordance with the disclosed subject matter.

Figure 16:
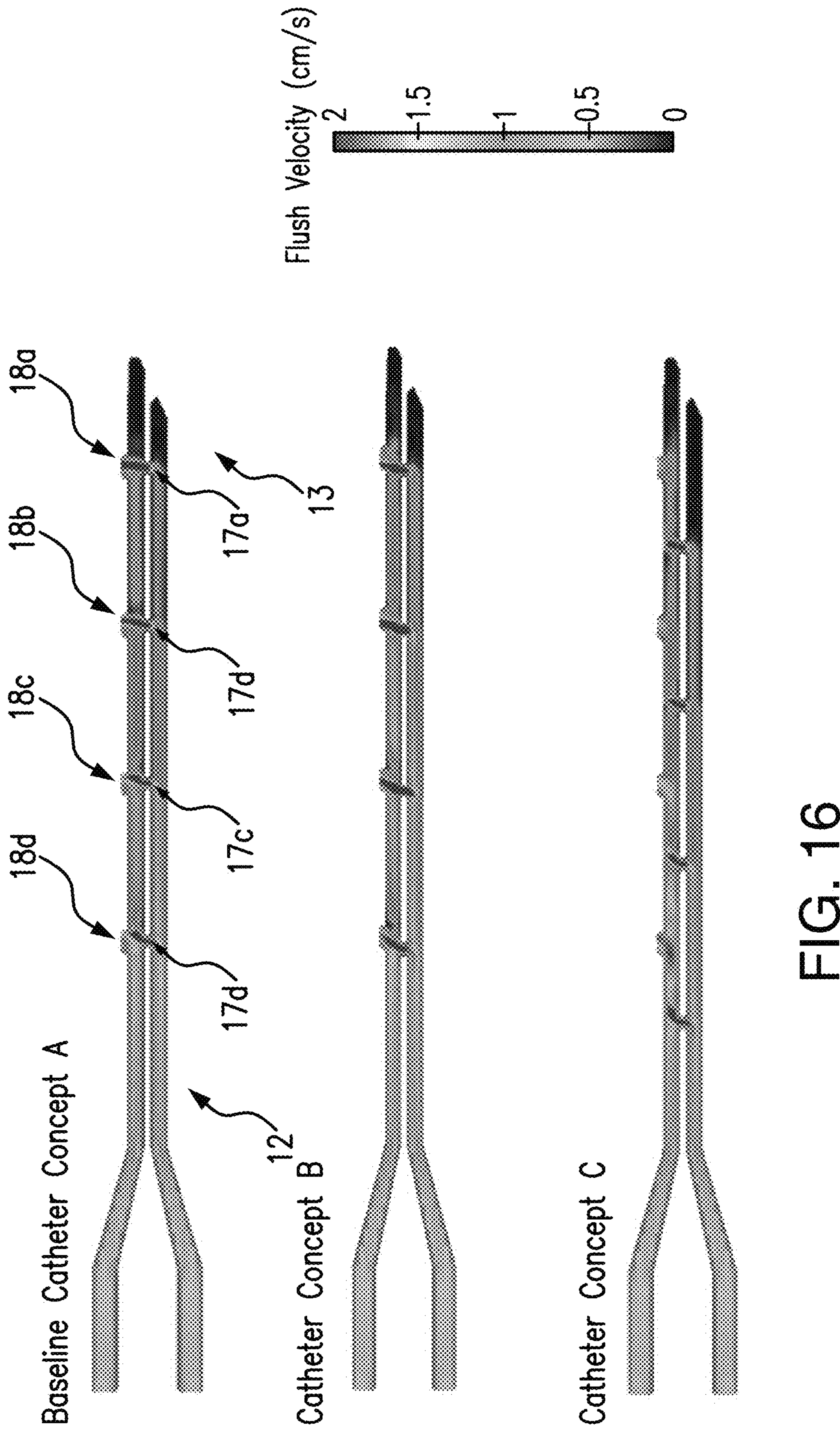

FIG. 16 illustrates exemplary results of computational fluid dynamics analysis of catheters having variable septal hole locations, in accordance with the disclosed subject matter.

Figure 17:
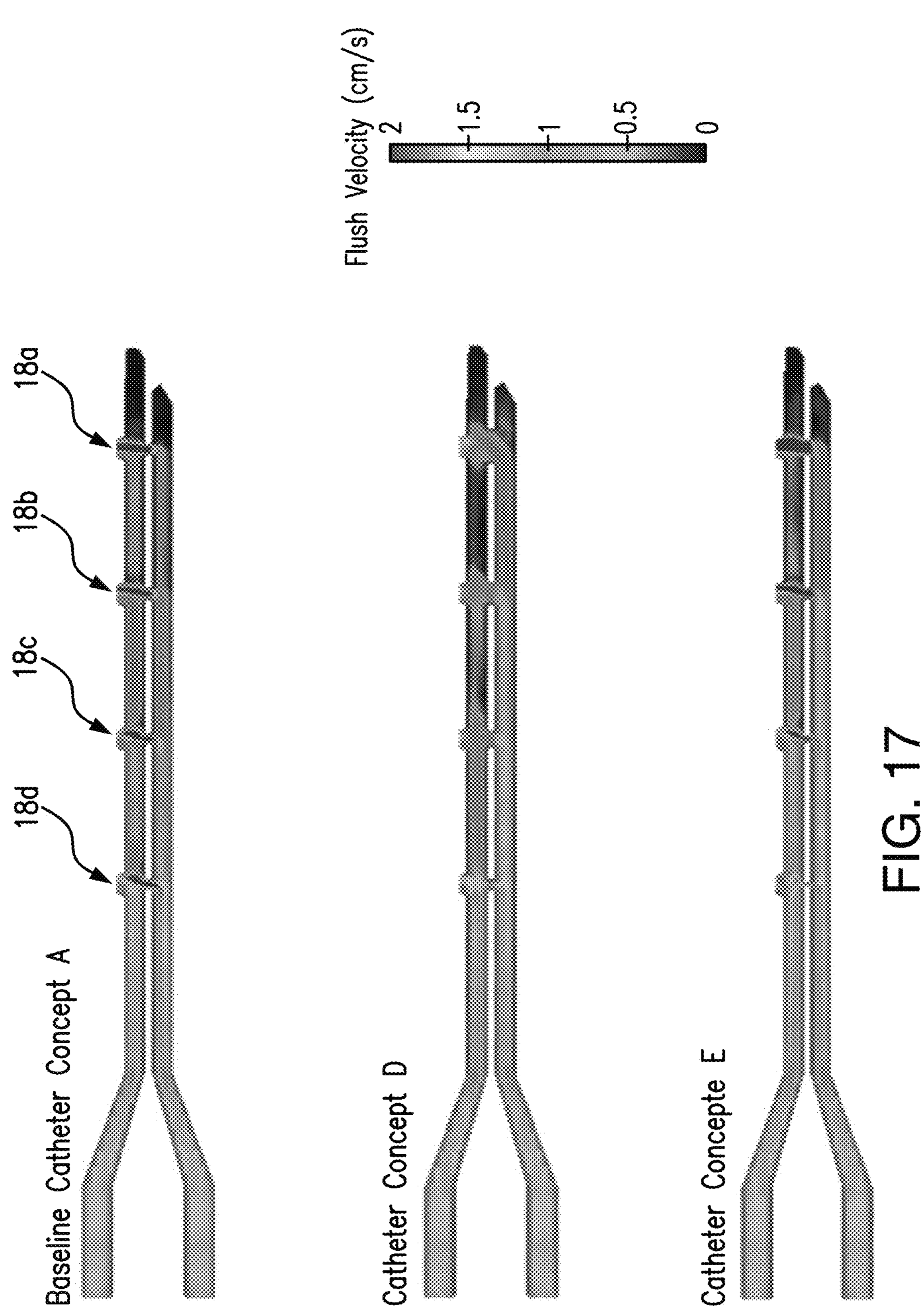

FIG. 17 illustrates exemplary results of computational fluid dynamics analysis of catheters having variable septal hole diameters, in accordance with the disclosed subject matter.

Figure 18:
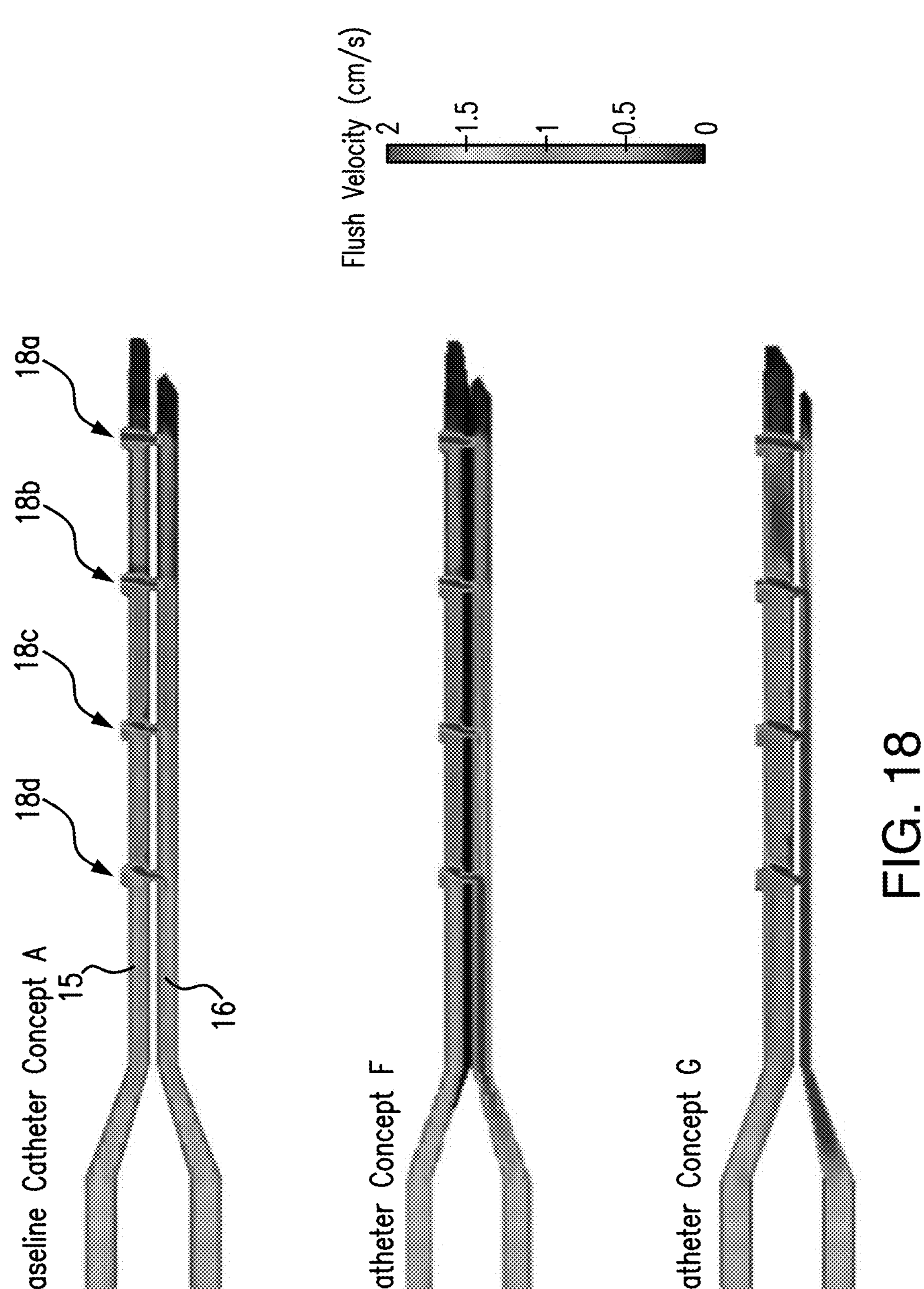

FIG. 18 illustrates exemplary results of computational fluid dynamics analysis of catheters having variable lumen volume ratios, in accordance with the disclosed subject matter.

Figure 19:
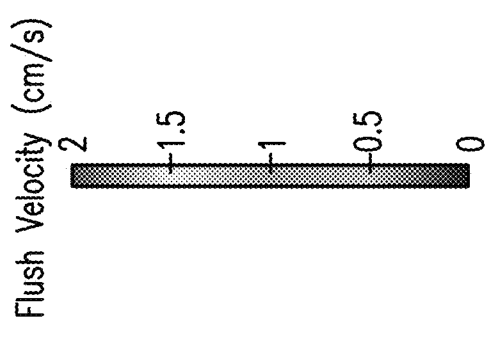
Figure 19:
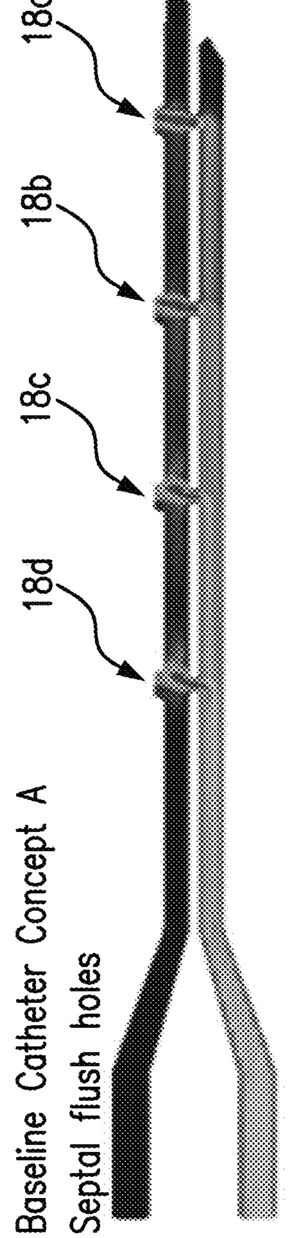
Figure 19:
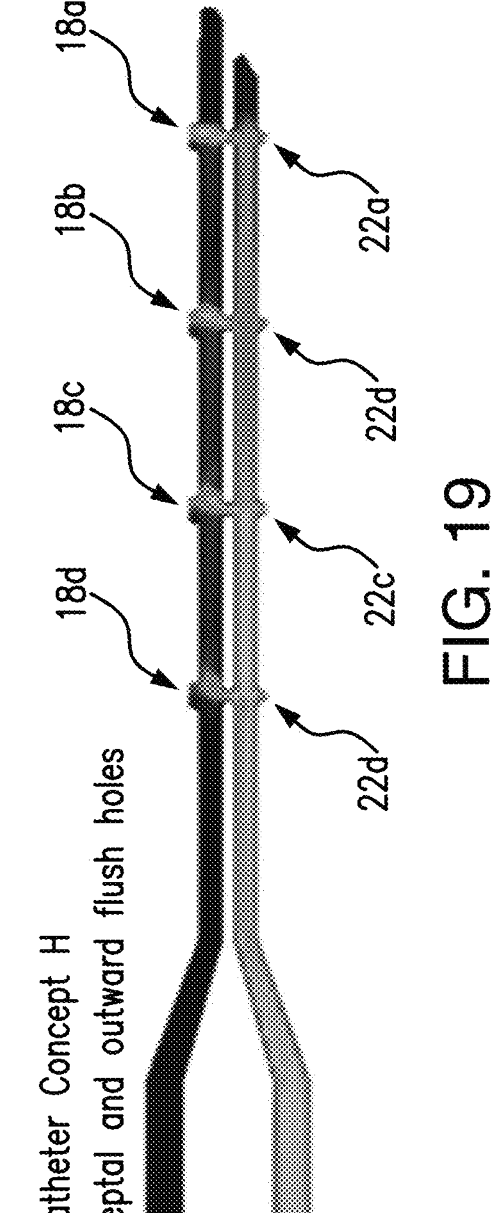

FIG. 19 illustrates exemplary results of computational fluid dynamics analysis of catheters with or without outward flush holes, in accordance with the disclosed subject matter.

Figure 20:
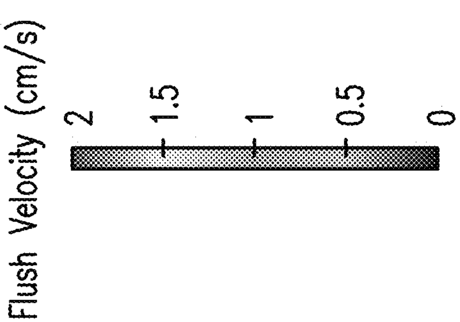
Figure 20:
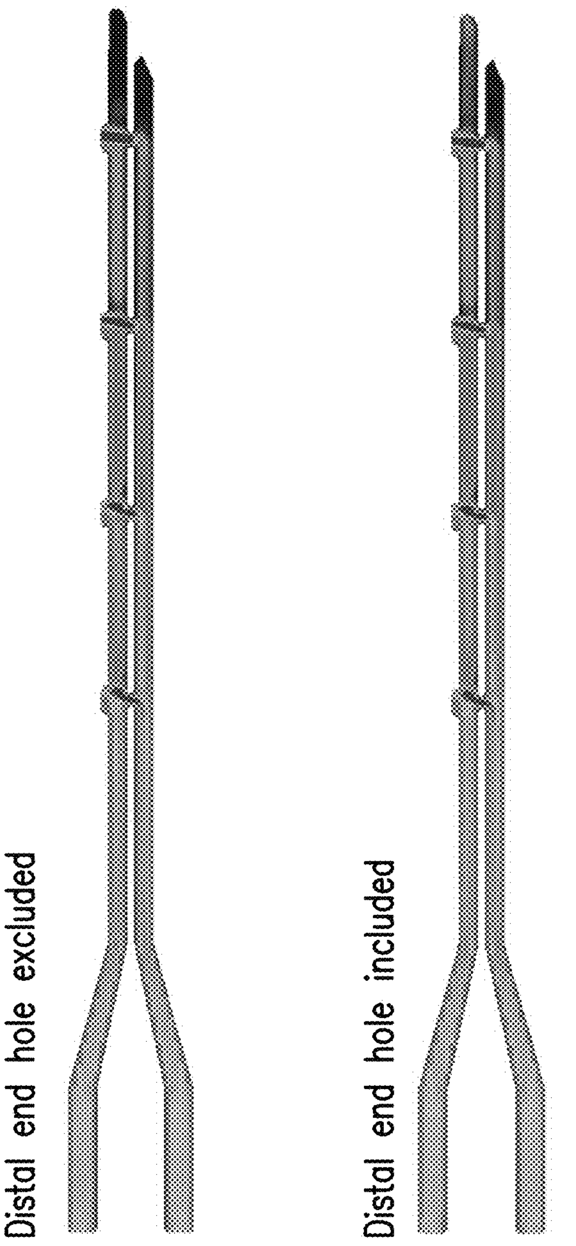

FIG. 20 illustrates exemplary results of computational fluid dynamics analysis of catheters with or without a distal end hole, in accordance with the disclosed subject matter.

FIG. 21 is a flow chart for a method for percutaneous drainage of a drainage site.

Figure 22:
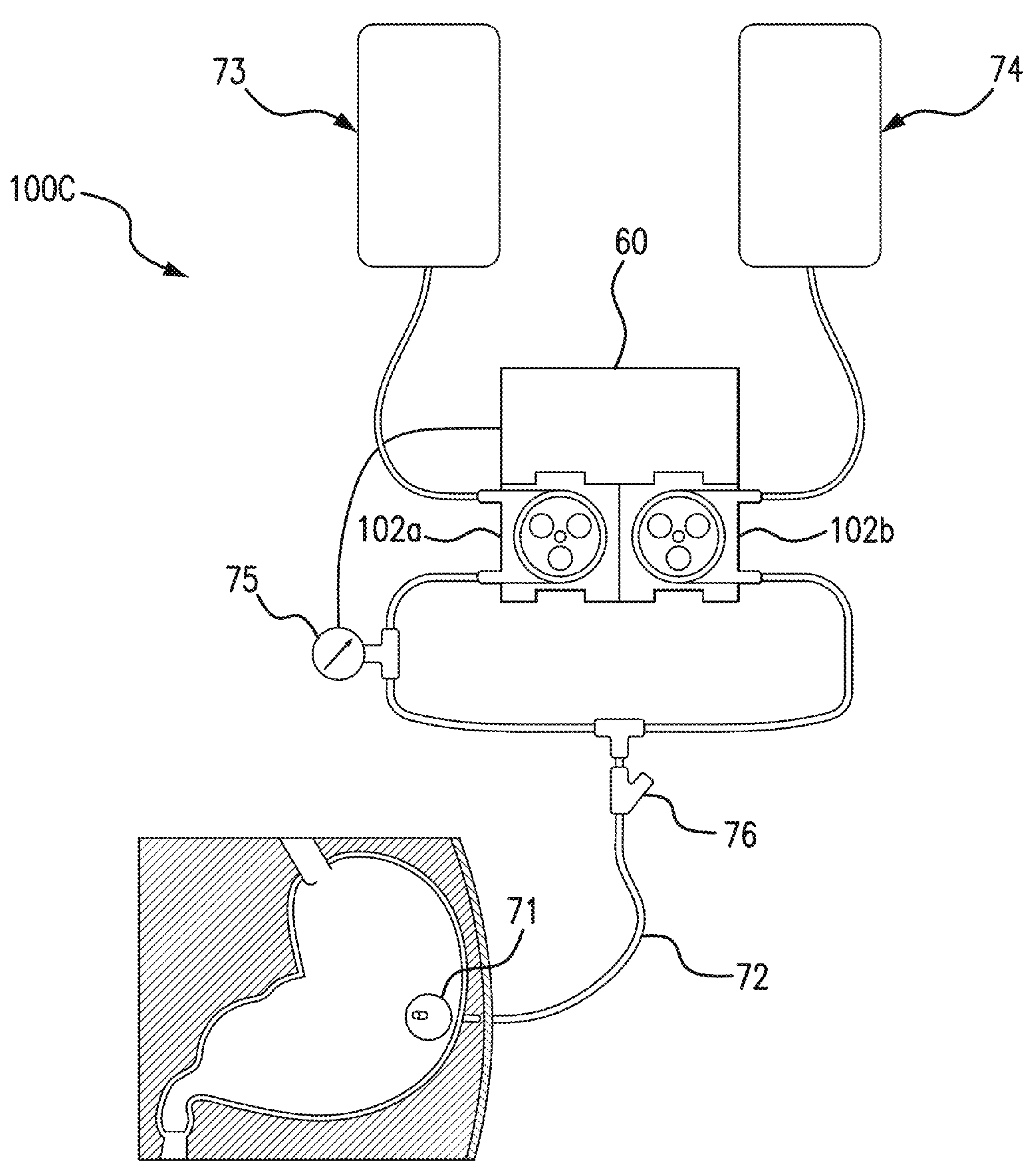

FIG. 22 is a schematic of an exemplary system for enteral feeding in accordance with the disclosed subject matter.

DETAILED DESCRIPTION

Reference will now be made in detail to the various exemplary embodiments of the disclosed subject matter, exemplary embodiments of which are illustrated in the accompanying figures. As used in the description and the appended claims, the singular forms, such as "a," "an," "the," and singular nouns, are intended to include the plural forms as well, unless the context clearly indicates otherwise.

Generally, and as set forth in greater detail below, the disclosed subject matter provided herein includes systems and methods for percutaneous drainage. For example, a system for percutaneous drainage of a drainage site includes a catheter, a drain tube, a first pump, a flush tube, a second pump, and a controller. The catheter includes a catheter wall extending from a proximal end portion of the catheter to a distal end portion of the catheter, the distal end portion of the catheter configured for placement within the drainage site, a septum disposed within the catheter wall and extending from a proximal end portion of the catheter to a distal end portion of the catheter, a drain lumen defined by a first portion of the catheter wall and the septum, and extending from the proximal end portion of the catheter to the distal end portion of the catheter, and a flush lumen defined by a second portion of the catheter wall and the septum, and extending from the proximal end portion of the catheter to the distal end portion of the catheter, wherein the flush lumen is separated from the drain lumen by the septum. The drain tube has a first end portion coupled to the drain lumen at the proximal end portion of the catheter, and a second end portion coupled to a waste collection container. The first pump is coupled to the drain tube between the first end portion of the drain tube and the second end portion of the drain tube. The flush tube includes a first end portion coupled to the flush lumen at the proximal end portion of the catheter, and a second end portion coupled to a flush material container having a flush material disposed therein. The second pump is coupled to the flush tube between the first end portion of the flush tube and the second end portion of the flush tube. The controller is coupled to the first pump and the second pump for controlling the first pump and the second pump. The septum has at least one septal hole disposed therein proximate to the distal end portion of the catheter such that the drain lumen and the flush lumen are in communication via the at least one septal hole. The catheter wall has at least one wall hole disposed therein proximate to the distal end portion of the catheter such that the drain lumen is in communication with the drainage site when the distal end portion of the catheter is placed within the drainage site.

Although systems and methods are described herein with respect to particular percutaneous drainage, such as abscess drainage, the systems and methods can be used for a wide variety of clinical applications common to fields of interventional radiology and/or surgery. For example, the systems and methods described herein can be used for percutaneous thoracostomy (i.e., pleural drainage of fluid (liquid and/or gas) and/or pleurodesis); percutaneous pericardiostomy (i.e., pericardial drainage); percutaneous nephrostomy, nephroureterostomy, and/or cystostomy (i.e., drainage and/or irrigation within the urinary tract); percutaneous cholecystostomy and biliary (internal-external, external) drainage; percutaneous chemical ablation and/or sclerosis of cystic lesions, recurrent fluid collections (such as lymphoceles and other disorders of the lymphatic system), and/or hollow viscera (such as gallbladder in candidates deemed unsuitable for cholecystectomy); percutaneous esophagostomy gastrostomy, gastrojejunostomy, jejunostomy, and/or cecostomy (i.e., the alimentary/digestive tract); percutaneous ventriculostomy and thecal sac drainage for hydrocephalus/CSF hypertension; and percutaneous thrombolysis/thrombectomy/embolectomy for thromboembolic disease of the arterial and/or venous vasculature.

As described in greater detail below, the systems and methods described herein can rapidly evacuate unwanted fluid from the body using a system of motorized pumps at a faster rate when compared to standard drainage catheters, which typically rely on gravity or manual suction bulbs. The system and methods can detect changes in catheter pressure dynamics and fluid volume transfer via programmable sensor indicative of various system states, such as impending luminal occlusion, satisfactory completion of drainage, and/or complications, such as hemorrhage, pneumothorax, or fistula formation. The system and methods can prevent and/or mitigate catheter occlusion via a self-flushing, dual lumen design using sterile saline and/or adjunctive chemical/biologic agents. Systems and methods described herein can include programmable aspiration/flush profiled tailored to the composition (e.g., volume, viscosity), of a fluid collection, and can remotely monitor and control drainage catheter system performance via wireless technology. This can allow healthcare providers and/or patients the ability to adjust pump settings, such as aspiration and/or flush rates, volumes, and/or frequencies. Furthermore, the systems and methods can collect and analyze biometric data (e.g., patient body temperature, which can indicate sepsis). The collected data can be used to guide therapeutic decisions. The systems described herein can be housed in a self-contained and powered wearable assembly with separate enclosures for electronics (e.g., pumps, circuit boards, power supply), sterile flush, and waste collection, with disposable components to allow for reuse.

Referring to FIGS. 1A-3 for purpose of illustration and not limitation, the disclosed system 100 can be configured for percutaneous drainage. The system 100 can include a catheter 10, a drain (also referred to as efflux, aspiration, and/or waste) tube 50, flush (also referred to as influx) tube 51, connector 52, a drain (also referred to as efflux, aspiration, and/or waste) pump 30, a flush (also referred to as influx) pump 40, a controller 60, a waste collection container 70, and a flush material container 71. The flush material container 71 can include a flush material 72. The flush material 72 can be saline, or other suitable flushing material. For example, sterile normal (0.9%) saline without or with one or more of the following: antimicrobial agents (e.g., antibiotic and antifungal medications) or therapeutic enzymes (e.g., tissue plasminogen activator [tPA], dornase, collagenase, and others) can be used. System 100 can include a remote device 67 in communication with the controller 60. The waste collection container 70 can have a pre-defined degree of baseline vacuum/negative internal pressure.

As described in greater detail below, the catheter 10 can be placed in a drainage site 2 of a patient. The system 100 can drain fluid from the drainage site 2 using a first lumen (e.g., the drain lumen 15 described below). The system 100 can maintain the patency of the first lumen by (1) using a second lumen (e.g., the flush lumen 16 described below) to periodically delivery a local diluent, and/or (2) reversing flow in the first lumen to dislodge occlusive debris, or both (simultaneously or non-simultaneously).

The catheter 10 can include a catheter wall 11 extending from a proximal end portion 12 of the catheter 10 to a distal end portion 13 of the catheter 10. The distal end portion 13 of the catheter 10 can be configured for placement in a drainage site 2. The catheter 10 can be a dual lumen catheter 10. For example, catheter 10 can include a septum 14 disposed within the catheter wall 11 and extending from a proximal end portion 12 of the catheter 10 to a distal end portion 13 of the catheter 10. A first portion of the catheter wall 11A and septum 14 can define a drain lumen 15 (also referred to as the efflux, aspiration, and/or waste lumen) and a second portion of the catheter wall 11B and the septum can define a flush lumen 16 (also referred to as the influx lumen). Each of the drain lumen 15 and the flush lumen 16 can extend from the proximal end portion 12 of the catheter 10 to the distal end portion 13 of the catheter 10. The volumetric proportions between the drain lumen 15 and the flush lumen 16 can be equal (i.e., 50-50; FIG. 3A), or unequal, for example, 80-20, 70-30 (FIG. 3B), 60-40 (FIG. 3B), or any other suitable ratio to achieve the desired flow dynamics. Although described as a particular dual lumen catheter (i.e., two lumens separated by a septum), any suitable dual lumen catheter can be used, including, for example, catheters with coaxial lumens, or with a septum that can be linear, curvilinear, or helical, twisting along the length of the longitudinal axis of the catheter, or two parallel cylindrical or hemicylindrical (or other shapes with flat edges) catheters fused along the length, either straight or where the lumens are twisted (intertwined) around along the long axis of the catheter. As another example, the drain lumen 15 or the flush lumen 16 can be incorporated into the catheter wall 11. Additionally, the drain lumen 15, flush lumen 16, catheter wall 11 and septum 14 can have any suitable shape to achieve the desired flow dynamics. The materials of construction of the catheter 10 can be any suitable materials that are biocompatible and amenable to thermoplastic extrusion, a common method for multi-lumen catheter construction. For example, the catheter 10 can be silicone, polyurethane, polyethylene, polyvinyl chloride, polytetrafluoroethylene, nylon, or thermoresponsive polymers. The catheter walls can be non-braided and/or braided with thin filament material.

Figure 2:
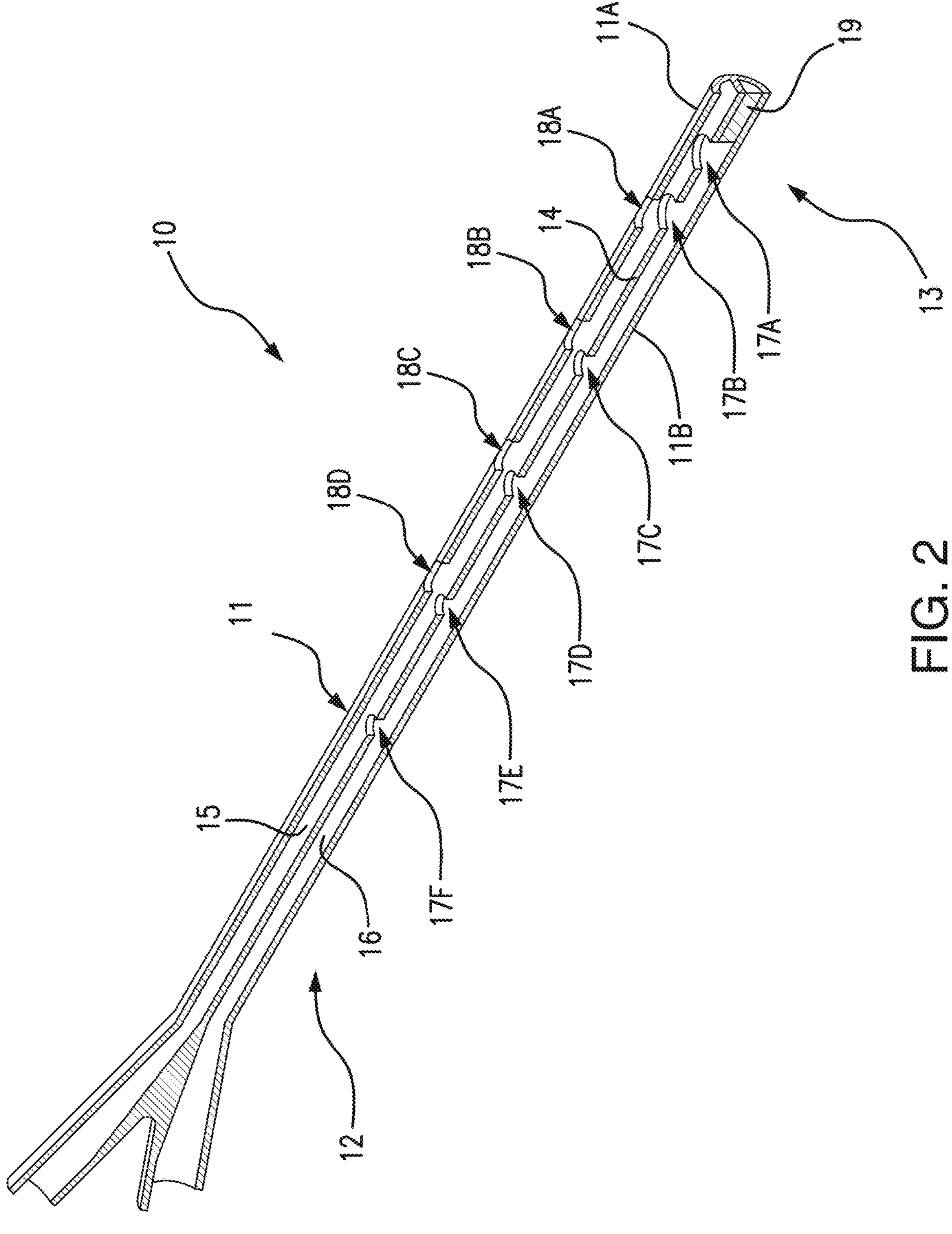
FIG. 2 is a cut-away view of an exemplary catheter for use with the system of FIG. 1A, in accordance with the disclosed subject matter.

The septum 14 can include at least one septal hole 17 (e.g., 17A-17F; also referred to as fenestrations) along its length such that the drain lumen 15 and the flush lumen 16 are in communication via the septal holes 17. For example, and as shown in FIG. 2 for purpose of illustration and not limitation, septum 14 can include six septal holes 17. The septal holes 17 can be disposed proximate to the distal end portion 13 of the catheter 10. The catheter wall 11 can include at least one wall hole 18 (e.g., 18A-D) along its length such that the drain lumen 15 is in communication with the drainage site 2 when the distal end portion 13 of the catheter 10 is placed within the drainage site 2. For example, and as shown in FIG. 2 for purpose of illustration and not limitation, catheter wall 11 can include four wall holes 18. The wall holes 18 can be disposed proximate to the distal end portion 13 of the catheter 10. Additionally, or alternatively, the drain lumen can have an open distal end hole to provide additional communication with the drainage site or to allow the catheter 10 to be delivered over a guidewire.

In an exemplary embodiment, the catheter 10 can include at least one wall hole 18 in the second portion of the catheter wall 11B along its length such that the flush lumen 16 is in communication with the drainage site 2 when the distal end portion 13 of the catheter 10 is placed within the drainage site 2. In such an embodiment, the septum 14 can be provided without septal holes 17 or with one septal hole 17. Such a catheter 10 can be used to deliver enzymatic and/or caustic agents such as detergent sclerosants to the injection site via flush lumen 16 which can lyse and/or otherwise break down complex components of a fluid collection, as well as iatrogenically induce an inflammatory response within the cavity to promote scarring and healing. The drain lumen 15 can be used to collect and remove the flush material, as well as the underlying pathologic fluid.

The wall holes 18 can be formed by any suitable means, for example, punches, drilling, or lasers. The septal holes 17 can similarly be formed by any suitable means. An inert and durable insert can be used when forming the septal holes 17 and/or wall holes 18 to prevent damage to the interior of the catheter wall 11 or septum 14, as appropriate (e.g., where holes are not intended). The septal holes 17 can be offset from the wall holes 18, for example, by delivering a puncturing tool at an angle through a wall hole 18 to the septum 14. For example, a puncturing tool that fits through wall holes 18 can be used to create septal holes 17. This can create septal holes 17 that can direct flush fluid back toward the wall hole 18 (for example, due to the relationship between septal holes 17A, 17B and wall hole 18A). Furthermore, the septal holes 17 can be cut with an angle, and as such, the septal holes 17 can direct the flush fluid back towards the corresponding wall hole 18 located just proximally of the septal hole 17. The septal holes 17 and the wall holes 18 can be placed at any suitable position along the septum 14 and catheter wall 11, respectively, and can be any suitable size or shape to provide the desired flow dynamics, as described in greater detail below. The size of the wall holes 18 and septal holes 17 can vary along the length of the catheter 10. For example, more distal septal holes 17 (e.g., 17A, B) can be larger than more proximal septal holes 17 (e.g., 17E, F). This can maintain roughly equivalent flow through the septal holes 17 along the length of the catheter. Alternatively, it can be desirable to provide higher rates of fluid flow through particular septal holes. Higher rates of flow through a particular septal hole can impact the patency of a corresponding or adjacent wall hole. For example, septal holes 17 can get progressively larger in diameter as fluid flows in the flush lumen 16 from the proximal end portion 12 of the catheter 10 to the distal end portion 13 of the catheter. Alternatively, distal septal holes 17 (e.g., 17A, B) can be smaller in diameter than proximal septal holes 17 (e.g., 17E, F). Although particular examples are described, any suitable septal holes 17 can be used to create communication between the flush lumen 16 and the drain lumen 15, and any suitable wall holes 18 can be used to create communication between the drain lumen 15 and the drainage site 2. Furthermore, it can be desirable to achieve greater flow velocity at wall holes 18A and 18B towards the distal end portion 13 of the catheter 10, as wall holes towards the distal end portion 13 can be more prone to clogging during use. Although particular septal holes 17 and wall holes 18 are described, any suitable septal holes 17 and wall holes 18 can be used to achieve desired flow dynamics. For example, holes with various sizes, gradients of sizes along the length, different shapes (e.g., ovals, slits, polygonal, circle) can be used. Walls of holes can be straight, tapered, rounded, or curved. Holes can be staggered or aligned along any aspect of the catheter (e.g., helical). Exemplary arrangements for septal holes 17 and wall holes 18 are provided in greater detail below.

The distal end portion of the flush lumen 16 can be closed. For example, a distal plug 19 or other suitable means for closing the distal end portion of the of the flush lumen 16 can be provided. The distal plug 19 can prevent flush solution (e.g., sterile solution) from exiting the distal tip of catheter 10, and can instead force the flush solution through the septal holes 17 into the drain lumen 15. This can increase pressure in drain lumen 15 and can dislodge material blocking the drain lumen 15 or wall holes 18. The flushing solution can also dilute more viscous bodily fluids to ease draining of the drainage site 2. The distal plug 19 and or the distal end of catheter 10, can be rounded to ease insertion through tissue and into the drainage site 2. Although a particular system for closing the distal end portion of the flush lumen 16 is described, any suitable means for closing the distal end portion of the flush lumen 16 can be used. The distal end portion of the drain lumen 15 can be open which can allow additional communication with the drainage site 2 and/or can be used for delivery using a guidewire, for example, using over-the-wire catheter insertion via the Seldinger technique.

Catheter 10 can have a straight, pigtail, looped, or other curved configurations. A combination of one or more configurations/curvatures can be included in series, and one or more configurations/curvatures can be repeated in series. The catheter 10 can be deformable to allow for placement in a first configuration and then to transition to a second configurations. For example, a shape memory material can be used to transition the catheter 10 to the second condition to keep the catheter 10 in place.

In accordance with the disclosed subject matter, catheter 10 can include a taper in size from a larger proximal portion 12 to a smaller distal portion 13, such that the body of the catheter can fully obturate the subcutaneous tunnel tract in the event that the distal portion 13 becomes dislodged from the drainage site 2. A tapered outer diameter can also prevent peri-catheter leakage. Additionally, or alternatively, catheter 10 can include a short length of ribbing and/or grooved threading on the outer wall 11 along its proximal-mid segment, which can allow for a securing device to anchor the catheter. For example, a non-absorbable suture can be used to affix the catheter securely to the skin without sliding along the catheter's length. Alternatively, an inflatable balloon, mushroom-shaped silicone dome, serrated ring, or deployable T-tacks, which can slide down the length of the catheter to the level of the skin aperture, can anchor the catheter 10 to the subcutaneous soft tissues.

Figure 1B:
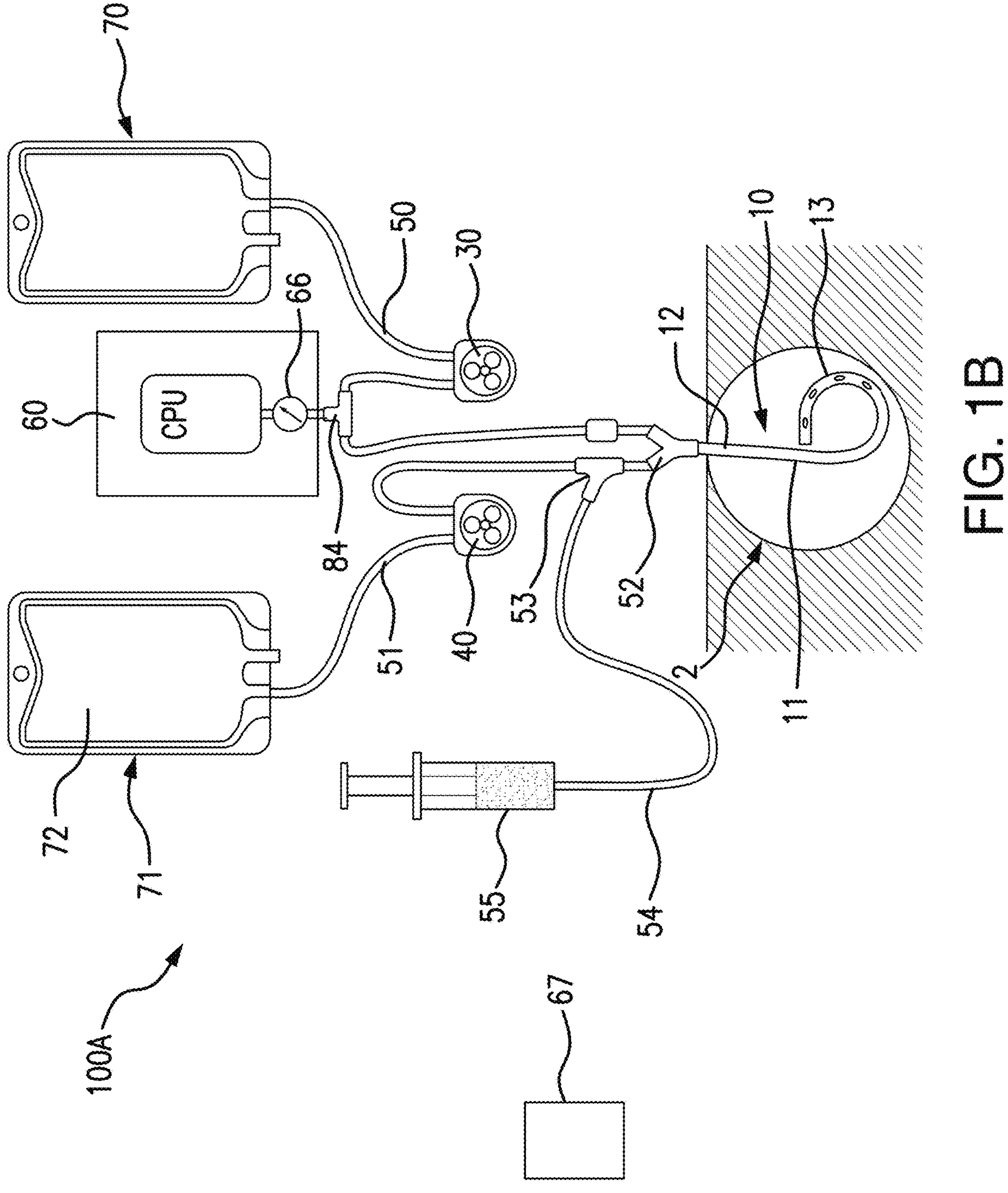
FIG. 1B is a schematic of an exemplary system for percutaneous drainage in accordance with the disclosed subject matter.

As shown in FIG. 1B, for purpose illustration and not limitation, system 100A includes each of the features of system 100, and further can include syringe injection port 53 coupled to flush tube 51 and third tube 54. Third tube 54 can be coupled to syringe 55 (or a third pump and reservoir). The syringe 55 can be used to deliver sclerosant, drugs, or other additional substances into the flush tube 51.

Referring to FIGS. 4-6 for purpose of illustration and not limitation, system 100 can include housing 80. The housing can be, for example, an enclosure for housing some or all electronic components of system 100. For example, housing 80 can house the drain pump 30, flush pump 40, and controller 60. The housing 80 can include a base 81 and cover 82. The base 81 and/or cover 82 can include mounting features 83 (e.g., 83A, 83B) for supporting the various electronic components. The mounting features 83 can be, for example, M3 heat-set inserts, which can be configured to receive M3×10 mm socket head cap screws (SHCS). Although particular mounting features are described, any suitable mounting features 83 can be used, for example, screws, nails, or adhesives. Cover 82 can be fastened to the base 81 by any suitable means, for example, M3×10 mm SHCS. When fastened together, the base 81 and cover 82 can create a protective and insulating housing 80 for the electronic components. The housing 80 can be sized and shaped such that the housing 80 can be carried, for example, inside a wearable pack (described in greater detail below).

The drain pump 30 and flush pump 40, which can be any suitable pumps, for example, 6V peristaltic pumps, can be mounted within the housing 80. Similarly, the controller 60, which can include any required or suitable electronics, such as a microcontroller 61 (for example, a Arduino Uno microcontroller), a motor driver 62 (for example, a L298N motor driver), a battery 63 (for example, a 200 mAh 9.6V Ni-MH battery), and an transmitter 64 (for example, an adafruit Bluefruit LE UART—Bluetooth Low Energy (BLE) transmitter) can be mounted within the housing 80. Although particular elements for the drain pump 30, flush pump 40, and controller 60 are described, any suitable elements can be used. The housing 80 can also house a breadboard 65, for example, on lid 82. The breadboard 65 can be used to route battery power from the battery 63 to the microcontroller 61 and motor driver 62, and can allow for modular, expandable off-board circuitry to be added as needed. Housing 80 can also include a pressure sensor 66 attached via a T-junction connector 84 to the drain tube 50. The housing 80 can include load transducers or liquid level sensors at the flush material container 71 and waste collection container 70 to measure fluid volume and evacuated fluid flow. The pressure sensor 66 can include a diaphragm seal and utilize MEMS sensors.

The base 81 and cover 82 can each have a slot 85, 86 (respectively), that can correspond with the positions of the drain pump 30 and flush pump 40, and allow for passage of the drain tube 50 and the flush tube 51 through both the base 81 and cover 82, such that the drain tube 50 and flush tube 51 can interface with the respective drain pump 30 and flush pump 40. For example, the drain tube 50 can extend from the waste collection container 70, through the slot 86 in cover 82, be routed to interface with drain pump 30, followed by T-junction connector 84, through slot 85 in the base 81, and then coupled to the drain lumen 15 at the proximal end portion 12 of the catheter 10 via connector 52. The flush tube 51 can extend from the flush material container 71, through slot 85 in cover 82, be routed to interface with the flush pump 40, through slot 85 in base 81, and then coupled to the flush lumen 16 at the proximal end portion 12 of the catheter 10 via connector 52.

Referring to FIG. 7 for purpose of illustration and not limitation, the battery 63 can provide power for one or more elements disposed in housing 80. The battery 63 can be removable from the housing, for example, for recharging or replacement. Battery 63 can be coupled to breadboard 65. A switch 69 can be provided between the battery 63 and the breadboard 65 for turning the device on and off. At breadboard 65, power can be distributed to the transmitter 64, microcontroller 61, and motor driver 62.

The microcontroller 61 can be used to provide logic for the transmitter 64, motor driver 62, drain pump 30, flush pump 40, and pressure sensor 66. For example, the microcontroller 61 can be an Arduino Uno board and can be programmed in C++ in Arduino Integrated Development Environment (IDE). The microcontroller 61 can be coupled to the pressure sensor 66 to receive pressure measurements of the drain tube 50. The microcontroller 61 can be coupled to the transmitter 64 to send and receive information (for example receiving operation instructions and sending pressure measurements or other measurements) to a remote device 67, such as a computer (such as a laptop or desktop computer), a personal data or digital assistant (PDA), or other user equipment or tablet, such as a mobile phone or portable media player. The communication between the transmitter 64 and remote device 67 can be wired or via one or more of a network, radiofrequency, or wireless connections, such as Bluetooth. The microcontroller 61 can also be coupled to the motor driver 62, which can be coupled to each of the drain pump 30 and the flush pump 40. Accordingly, the micro controller can send control signals to the motor driver 62 (for example in the form of digital signals) and the motor driver 62 can send the signals, for example, pulse or step signals and direction signals (for example in the form of pump voltages) to the drain pump 30 and the flush pump 40. Although particular arrangements are described, any suitable arrangements can be used for the electronic components to achieve the desired drainage and flushing.

Referring to FIG. 8, for purpose of illustration and not limitation, the housing 80 can be sized to fit within a wearable component 90, such as a belt-mounted pouch 91. The belt 92 can be adjustable and can make it possible for the patient to carry system 100 with relative ease. The pouch 91 can be designed to fit the housing 80 and can include holes or slots such that the flush tube 51 and waste tube 50 can extend through the pouch 91. Two external containers 93, 94 can be available in assorted sizes which can be attached via holsters directly to the belt, or into built-in pockets in the pouch 91. The external containers 93, 94 can hold the flush material container 71, and the waste collection container 70, respectively. Although a particular wearable component is described, any suitable wearable component can be used.

In nominal operation, the catheter 10 can be delivered to the drainage site 2. Instructions can be provided from the microcontroller 61, via the motor driver 62, to operate drain pump 30 to engage the drain tube 50 and to withdraw fluid from the drainage site through the wall holes 18, through the drain lumen 15, through the drain tube 50 and into the waste collection container 70 (also referred to as the drain line). Unidirectional (e.g., duckbill) valves can be used within the various elements of the drain line and/or at the joints, to prevent backflow and/or leakage of waste fluid. During draining, the pressure sensor 66 can continuously (or intermittently) measure the pressure in the drain tube 50 and can provide a continuous voltage to the microcontroller 61. An average value can be taken over a buffer, for example, 10 pressure sensor measurements at approximately 1000 Hz. If a clog forms in the drain path (i.e., in the wall holes 18, drain lumen 15, or drain tube 50) the average pressure value can rise above a threshold. The threshold can be, for example, a user defined threshold. The system 100 can recognize that the increase in average pressure indicates a clog and a flush operation can be initiated. For example, the microcontroller 61 can send a signal, via motor driver 62, to stop drain pump 30. The microcontroller 61 can send a signal, via motor driver 62, to start or increase flush pump 40 to pump the flush fluid from the flush material container 71, through flush tube 51, through flush lumen 16, and through septal holes 17 (also referred to as the flush line). Additionally or alternatively, the microcontroller 61 can send a signal, via motor driver 62, to reverse direction of the drain pump 30. These actions can flush clogs that can form in the wall holes 18, the drain lumen 15, and/or drain tube 50. The microcontroller 61 can control the rate of reverse flow in the drain line, for example, the flush volume can be programmed to be equivalent to the length of the drain lumen 15 and the drain tube 50. This can prevent reintroducing existing waste material into the body that has been residing in the waste collection container 70. After the flush operation is performed, the microcontroller 61 send signals, via motor driver 62, to stop the operation of the flush pump 40 and to resume operation of the drain pump 30 to resume the draining process. Another measurement buffer can be used to prevent multiple flushes in a short duration while the pressure readings stabilize. In system 100*a* of FIG. 1B, the microcontroller 61 can further control syringe 55 (or third pump) for delivery of additional solutions (e.g., sclerosant/drugs) into the flush tube 51, into the flush line.

The remote device 67 can communicate with the transmitter 64 via a wireless transmission, such as a Bluetooth connection. For example, an Adafruit Bluefruit library can be used. A companion application (for example for use on an android operating system) can be developed in Java using Android Studio. The application can allow for Bluetooth connection to the microcontroller 65 (via the transmitter 64), which can enable different device settings that are optimized for the patient or medical condition settings to be selected and customized by a user (for example a clinician) on the application. For example, pump speeds, flush frequency, and flush volume can be adjusted using the application. Preset device configurations and settings for different medical conditions, tubing diameters, and catheter dimensions can be designated in the application inputted to improve ease of use and specificity. Additionally, schedules can be programmed by the user to control flush frequency, which can periodically flush the catheter 10 even if no clog is detected. The application also provides access to manual pump actions without necessitating the detection of a clog, such as flushing the system or reversing the flow upon selection in the application. The application can be controlled via a graphical user interface 68 (FIGS. 9A-C) or alternatively with physical controls (e.g. touchscreen) integrated with hardware.

Statistics and information can be collected and stored within the controller 60. For example, biometrics and fluid drainage statistics (e.g., abscess volume drained, pressure generated during aspiration) can be collected and stored. The fluid drainage statistics can be used to notify users via the application when the waste collection container or flush material container is full or empty, respectively, and needs to be replaced. The controller 60 can be reset before each use. Algorithms can be performed on the microcontroller 65, such as regression equations to calculate how much abscess volume has been drained using the pump speed and duration. The information can be transferred to the remote device 67 (e.g., via Bluetooth, Wi-Fi, cellular network, or radio frequency) and accessed by a user. The information can then be used for further diagnosis and additional and/or new instructions can be provided via the remote device 67. For example, a slow and consistent drop in change in pressure can indicate that the abscess is collapsed or healed, while a sudden increase in change in pressure can indicate a clog (e.g., a fistula) may be forming or a catheter malfunction. Accordingly, an alert can be provided to a health care provider.

Additionally or alternatively, additional programmable features can be provided. For example, simultaneous pump function in real time, alternating function, reversal of pump functions, changing high/low pressure settings, sensor thresholds, can allow customization of pump behavior and settings. Aspiration/flush settings can be configured to automatically adjust/adapt to the mechanical properties of the waste fluid, occlusive luminal debris, and transduced pressure within the drainage site 2. For example, the system can operate differently depending on the fluid to be drained, including air (pneumothorax), thin serous fluid (e.g., seroma, urine, ascites, pleural fluid, cysts), intermediate viscosity fluid (e.g., pus from abscess/empyema, non-infected bile, infected urine), and thick viscosity fluid (e.g., infected bile, liquefying hematoma, superinfected necrotic tissue, pancreatic pseudocyst, ruptured bowel contents). For example, pressurized pulsed sterile saline lavage can be used to irrigate a complex collection and liquefy its contents.

Additionally or alternatively, an integrated suite of patient biometric sensors (e.g., body temperature, heart rate, blood pressure, glucose level, hydrations status, or other biometric information) can be provided and can further influence system function. Real time data can be transmitted to a HIPAA secure web site (in addition or as an alternative to the remote device 67), that health care provides can monitor and that can provide alter notifications for significant changes in health status. For example, rate of change in fluid flow rate, total aspirated fluid volume/time, pressure within the catheter 10 and/or body cavity can be monitored and transmitted. Slow and progressive decrease in daily fluid output can indicate medical outcomes for the patient, such as resolution of abscess, resolution of pneumothorax without further air leak allowing for thoracostomy tube removal, patency of cystic duct allowing for cholecystostomy tube removal, patency of ureter allowing for PCN/PCNU removal. Rapid rise in body cavity pressure and resistance to flow can indicate hemorrhage. Rapid drop in body cavity pressure can indicate fistula formation. Biofeedback data can be used in conjunction with artificial intelligence and machine learning techniques to better predict and manage drain function for particular types of fluid collections, anticipated resolution of drainage, and patient health risk level. Although particular examples of data and methods of storage, transmitting, and using the data are described, any suitable data can be measured, stored, transmitted, or relied upon.

In accordance with the disclosed subject matter, pre-filled cartridges including chemical/enzymatic agents which can be injected into the flush line to dissolve intraluminal debris and/or antimicrobial medications can be provided. For example, one or more of tissue plasminogen activator (tPA), donase, collagenase, sterile weak acid solutions, or antibacterial/anti-fungal drugs can be provided. Additionally or alternatively, catheter vibration via a high frequency oscillator attached to the catheter 10, embedded piezoelectric crystals for sonolysis, and/or other mechanisms can be used to maintain luminal patency. Integrated bioagent assays can be provided to determine the specific chemical composition of the waste fluid being removed.

Multiplex System with One or More Catheters and/or One or More Pumps

In accordance with the disclosed subject matter, a plurality of catheters 10 can be provided to a single patient, and one or more control systems (for example, a single CPU) can manage each catheter 10. For example, a patient can receive a plurality of drainage catheters and a single central receiver can manage and/or coordinate the variable functions of each drainage catheter 10 (e.g., monitor for blockage, determine when to flush, monitor patient conditions). Additionally, systems can be modularly stacked, assigning one system to each fluid collection, which can minimize ergonomic burden on the patient, and can facilitate management.

Referring to FIG. 10, an individual patient with multiple separate abscesses 200A, 200B or a single multiloculated abscess, may require insertion of multiple drainage catheters 10A, 10B for adequate fluid evacuation. When the system is used for treating multiple separate abscesses, or a single multiloculated abscess, the system can be multiplexed to allow for either simultaneous suction and flushing of multiple catheters, or alternating drainage that switches between catheters. This multiplicity function can allow a single system to automatically control multiple drainage and/or feeding catheters in an individual patient via its controller logic, or add more pumps to the system in a modular fashion. For example, valve 103, illustrated as a three-way stopcock between catheters 10A an 10B, can alternate drainage between two or more catheters draining multiple abscesses or a single complex abscess. The valve 103 can switch between a first and second state. In the first state as shown in FIG. 10, fluid is in communication from the first abscess 200A across the valve 103 to the waste collection container 70. In the first state waste can be removed from the first abscess 200A, but not the second abscess 200B. In a second state (not shown), fluid is in communication from the second abscess 200B across the valve 103 to the waste collection container 70. In the second state waste can be moved from the second abscess 200B, but not the first abscess 200A. Additionally or alternatively, the valve 103 is operated automatically by the controller 60.

In accordance with the disclosed subject matter, a plurality of pumps and/or valves can be regulated by a central control unit. For example, multiple drain and flush pumps can be multiplexed to allow for either simultaneous suction and flushing of multiple catheters, or alternating drainage that switches between catheters. Alternatively or additionally, multiple valves can be switched under the control of the central control unit. The central control unit regulates the action of the multiple pumps and/or valves.

Regarding the plurality of pumps, multiple pumps can be plugged into a central control unit, which can then power and individually control each modular pump. Referring to FIG. 11, the central control unit 101 acts as a hub, which provides power and coordinates the actions of each individual pump (102*a*, 102*b*, 102*c*, 102*d*). Individual pumps can be identified by unique numerical designations to ensure that the correct individual pump is programmed accordingly and that the correct line (either serving as suction or flush) is secured to the particular individual pump. Each individual pump can be attached to either the waste collection container 70, or the flush material container 71 depending on its role. The central controller unit 101 allows the individual pumps to be programmed independently. Individual pumps (e.g., 102*a*, 102*b*) can be plugged into the central control unit 101 to receive power and communication via direct connection. Additionally, individual pumps (e.g., 102*c*, 102*d*) can be plugged into pumps 102*a* or 102*b* to receive power and communications passed through another pump. Additional pumps could be added in accordance with the disclosed subject matter. For example, when adding two additional drainage catheters, up to four individual pumps can be added to the system.

Regarding the plurality of valves, additional valves can be placed between a pump and the catheter. These plurality of valves can be regulated by the control unit 101, and the plurality of valves can switch between two or more different states to service two or more separate catheters. Depending on the position of the valve, fluid can either be permitted or prevented from flowing across the valve, thus allowing for the variable application of suction or flush to an individual catheter. Referring back to FIG. 10, for purpose of illustration and not limitation, draining the first abscess 200A using suction generated by peristaltic pump 102, the valve 103 can switch between two states dictated by the control unit 101. For example, switching valve 103 can alternate between the first catheter 10A and second catheter 10B placed in the first and second abscesses 200A, 200B, respectively. Alternatively or additionally, the peristaltic pump 102 can alternate pumping with periodic flushing, or flush on demand if a clogged state has been detected in the line.

Experimental Results: Effects of Periodic Flushing on Suction Performance

In accordance with the disclosed subject matter, drainage performance of the system disclosed herein using three different suction conditions was compared. Catheter 10 having flush lumen 16, drain lumen 15, and septal holes 17 for flushing external drainage wall holes (e.g., 18A-D) from across the septum 14 was used. Flushing across septum 14 can dislodge debris obstructing the at least one external drainage wall hole 18A-D and locally dilute abscess material to maintain luminal patency of the catheter 10. The catheter as embodied herein was tested using three different suction conditions: (1) suction provided by a Uresil accordion suction bulb, (2) suction only from a peristaltic pump, and (3) suction with periodic flushing from a peristaltic pump. An abscess analog composed of fruit blended in dairy was used. Under condition (3), when flushing was provided in addition to the suction, 10 mL of water was flushed through the catheter over an 18 second period every 2 minutes by a second peristaltic pump. Furthermore, the disclosed catheter was tested with water under the three different suction conditions as a control. All three suction conditions drained 100 mL (100 g) of water in under 5 minutes (data not shown).

Referring to FIG. 12, the results of suction over 20 minutes through the draining catheter as disclosed herein using the three different suction conditions is shown. Using the catheter as disclosed herein, after 20 minutes of draining the abscess analog, the Uresil accordion bulb removed 4.0+/−2.1 g of material, the peristaltic pump without flushing removed 61.0+/−6.3 g of material, and the peristaltic pump with periodic flushing removed 81.4+/−3.8 g of material. The peristaltic pump drained approximately 15× the abscess material over the first twenty minutes compared to the accordion bulb. Periodic flushing resulted in a 33% improvement over the same time frame using the same modality of suction. When using the Uresil accordion bulb suction and peristaltic suction alone (i.e., without flushing), rapid obstruction of the four drainage holes was observed within this time frame, and subsequent priming of the accordion bulb (data not shown) had little to no effect. If suction power was to remain insufficient to pull the material through the four 2 mm diameter drainage holes, the catheter would remain obstructed and drainage would cease or be significantly diminished unless cleared via flushing.

Further referring to FIG. 12, standard error is shown in the shaded regions and average mass drained is shown for each of the three suction conditions. Periodic flushing can clear obstructions from the external drainage holes while locally diluting viscous material. In current medical practice, flushing is performed manually and infrequently (e.g., once every 8 hrs). Increasing manual periodic flushing is not practical in the clinical setting. However, automated periodic flushing of the external drainage holes using a multi lumen catheter with septal holes, as demonstrated here, can improve drainage at equivalent suction pressures.

Computational Fluid Dynamics (CFD) Analysis and Results: Catheter Structure Evaluation In accordance with the disclosed subject matter, computational fluid dynamics (CFD) analysis of the disclosed catheter was used to evaluate different catheter structures without the need for physical prototypes. CFD can determine parameters that evenly distribute the flush flow profile throughout the external drainage wall holes. As blockages can occur irregularly across the catheter external draining or septal holes, it is important to flush uniformly throughout the length of the catheter to minimize the probability of occlusions leading to catheter failure.

For example, through iterative, simulation prototyping, different catheters were quickly modeled and evaluated for flushing performance as measured by flow rates through the catheter external drainage and septal holes. All 3D models of the dual-lumen catheter were created using 3D parametric modeling software, Fusion 360 (Autodesk, San Rafael, CA, United States)). Using geometric modifiers, structural features of the catheter were parametrically manipulated to generate the catheter structural concepts. Referring to FIG. 13, the original baseline catheter structure (Concept A) consisted of a dual lumen channel with four external drainage wall holes 18*a*-18*d* (2 mm diameter) spaced 13 mm apart, and 4 septal holes 17*a*-17*d* (1 mm diameter) that were equally sized and aligned with wall holes 18*a*-18*d*. The distal tip of catheter 10 can be tapered, with a small opening that mimics the guide hole commonly found in multipurpose drainage catheters. The distal opening 21 allows for direct communication with the waste lumen 15, and indirect communication to the flush lumen 16. In the CFD analysis, fluid flow through distal opening 21 was ignored as the size and location only marginally impacted the fluid dynamics.

Again referring to FIG. 1A, catheter 10 has two reversible pumps attached to both the flush and waste lumen which can be independently controlled. The typical flushing action can be coupled with a brief reversal of the suction pump at an equivalent fluid velocity to generate greater positive flow, and hence pressure, at the wall holes 18*a*-18*d* to clear debris. Regarding FIG. 15, the baseline catheter Concept A structure was used to compare various flush pumping and/or suction pumping techniques. Using CFD, a saline flush only, and a simultaneous saline flush and suction pump reversal action was performed, and CFD differences were quantified. Additionally, the simultaneous flush and suction pump reversal was compared to a saline flush only technique at twice the flush velocity to measure how average flow rates at the wall holes 18*a*-18*d* compared when the flush fluid flow is (a) either split across both waste 15 and flush 16 lumens, or (b) only the flush lumen 16. Running both the flush pump and suction pump simultaneously was used to analyze all ensuing structural modifications.

Subsequent structural modifications to the catheter geometry improved flushing performance. These structural modifications included alignment of septal holes to the distal holes, varying septal hole diameter, and cross-sectional area of waste and flush lumens. All concepts were compared to the baseline catheter structure (Concept A) to assess increases/decreases in wall hole fluid velocity during flushing. Table 1 summarizes the various catheter structures tested.

Regarding Concepts B and C, the location of septal holes 17*a*-17*d* were staggered with respect to the wall holes 18*a*-18*d* along the catheter. It was theorized that fluid interference at the junctions between the flush liquid and reversal from the waste lumen could be compensated through alternative positioning, improving wall hole flow. Regarding Concepts D and E, the diameters of septal holes 17*a*-17*d* were varied such that the septal holes diameters increased from septal hole 17*d* by the proximal end portion 12, towards septal hole 17*a* by the distal end portion 13. Furthermore, in Concepts F and G the waste lumen to flush lumen volume ratio was increased to investigate if the augmented venturi effect could improve flushing. Catheter Concept A-G structures are provided in Table 1.

TABLE 1

Summary of Structural Changes Relative to Baseline Catheter (Concept A). CFD analysis proceeded for Catheters Concepts B-G simulating changes in volume ration, septal hole diameter, and septal hole location.

| Concept | Volume Ratio (Waste Lumen:Flush Lumen) | Septal Hole Diameter (mm) (17d, 17c, 17b, 17a) | Septal Hole Location |
|---|---|---|---|
| A (Baseline Catheter) | 50:50 | 1, 1, 1, 1 | Aligned with outlet holes |
| B | 50:50 | 1, 1, 1, 1 | Septal holes shifted proximally 1 mm |
| C | 50:50 | 1, 1, 1, 1 | Septal holes shifted proximally 6.5 mm |
| D | 50:50 | 1, 1.5, 2, 3 | Aligned with outlet holes |
| E | 50:50 | 0.5, 0.75, 1, 1.5 | Aligned with outlet holes |
| F | 60:40 | 1, 1, 1, 1 | Aligned with outlet holes |
| G | 80:20 | 1, 1, 1, 1 | Aligned with outlet holes |

CFD Methods and Procedure

To perform CFD analysis, the 3D CAD models of the proposed catheter designs were imported into OpenFOAM CFD software (The OpenFOAM Foundation, United Kingdom). In OpenFOAM, finite element models were generated for catheter Concepts A-G at approximately a 5:1 scale. Scaling models is common approach to reducing the simulation complexity and decreasing time to complete CFD simulations. The fluid dynamics at the flushing phase of the device was visualized and quantified across all catheter design concepts. In OpenFOAM, a simple steady-state fluid flow simulation was performed across catheter Concepts A-G. Regarding FIG. 14, a finite volume method was applied to solve basic Navier-Stokes equations and show streamlines. In these simulations only conservation of mass and momentum equations were applicable as no heat transfer was assumed. Homogenous liquid properties for water were used in both inlets, assuming an incompressible liquid flow. The flush inlet velocity was defined at 1.5 cm/s for the flush flow. When examining the flush and suction pump reversal, the flush inlet velocity of 1.5 cm/s was duplicated at the waste lumen inlet. Catheter performance between design concepts was assessed by measuring the steady state fluid velocities at the outlets during flushing. Specifically, the average fluid flow velocity across the surface area of the external drainage wall holes 18*a*-18*d* were calculated.

Iterative CFD Comparative Analysis: Saline Flush Simulations

Regarding FIG. 15 and corresponding Table 2, in a saline flush simulation, there was a substantial increase in all wall hole velocities (18*a*-18*d*) for simultaneous flush and suction pump reversal when compared to flushing only. Fluid flow increased by 147%, 102%, 79%, and 82% for wall holes 18*d*, 18*c*, 18*b*, and 18*a*, respectively. The flush and suction pump reversal closely approximated the flow velocity observed during a saline flush at twice the initial fluid velocity. The decrements between these two conditions were less than 16% across all wall holes. Thus, all subsequent CFD design evaluations would only use the saline flush and waste flow removal mechanism. Table 2 illustrates the results from the baseline catheter (Concept A) used for the three tests in FIG. 15. Regarding Table 2, the baseline catheter was analyzed with a saline flush only, saline flush and simultaneous suction (i.e., fluid flow reversal) in the drainage lumen, and saline flush only at twice the velocity.

TABLE 2

CFD results for saline flush and/or simultaneous pump simulations of Baseline Catheter (Concept A).

| Baseline Catheter (Concept A) | Wall Hole 18d (cm/s) | Wall Hole 18c (cm/s) | Wall Hole 18b (cm/s) | Wall Hole 18a (cm/s) |
|---|---|---|---|---|
| Saline flush only | 0.38 | 0.54 | 0.72 | 0.78 |
| Saline flush and suction pump reversal | 0.94 | 1.09 | 1.29 | 1.42 |
| Saline flush only at twice velocity | 1.02 | 1.26 | 1.5 | 1.57 |

Iterative CFD Comparative Analysis: Septal Hole Shifting (Concepts B and C)

Regarding FIG. 16 and corresponding Table 3, septal holes 17*a*-17*d* were shifted towards proximal end portion 12 and the catheter performance was reviewed. Shifting septal holes 17*a*-17*d* 1.0 mm towards proximal end portion 12 in Catheter Concept B, can increase fluid velocities at all outlet wall holes 18*a*-18*d* in comparison to the baseline catheter Concept A. Shifting septal holes 17*a*-17*d* 6.5 mm towards proximal end portion 12 in Catheter Concept C can increase fluid velocity in proximal most wall holes 18*d* and 18*c*, but decrease fluid velocity in distal most wall holes 18*b* and 18*a*. Regarding Table 3, the fluid velocity variations across outlet wall holes 18*d*, 18*c*, 18*b*, and 18*a* were +43%, +17%, −2%, and −13%, respectively. The largest fluid velocity increase in Concept B was observed in outlet 18*d* with a 15% increase.

TABLE 3

Concept Catheter Structures B and C wall hole flow velocities compared to Baseline Catheter (Concept A): Changes in fluid velocity at the wall holes 18a-18d as a function of shifting septal holes (e.g., 17a-17d; FIG. 13) towards proximal end portion 12 compared to the baseline catheter Concept A.

| Catheter Design Concept | Wall Hole 18d (cm/s) | Wall Hole 18c (cm/s) | Wall Hole 18b (cm/s) | Wall Hole 18a (cm/s) |
|---|---|---|---|---|
| Concept A: Baseline Catheter | 0.94 | 1.09 | 1.29 | 1.42 |
| Concept B: Septal Holes Shifted Proxmally 1 mm | 1.08 | 1.18 | 1.38 | 1.43 |
| Concept C: Septal Holes Shifted Proxmally 6.5 mm | 1.34 | 1.28 | 1.27 | 1.23 |

Iterative CFD Comparative Analysis: Septal Hole Diameter Modifications (Concepts D and E)

Regarding FIG. 17 and corresponding Table 4, in Concepts D and E, the septal holes 17*a*-17*d* had their diameters modified and the CFD results were evaluated. In catheter Concept D, the septal hole diameters of septal holes 17*d*, 17*c*, 17*b*, and 17*a* were changed from 1 mm for all septal holes in the baseline catheter, to 1, 1.5, 2, and 3 mm, respectively. Compared to baseline catheter Concept A, the fluid velocity at proximal most wall holes 18*d* and 18*c* of catheter Concept D increased, but the fluid velocity at distal most wall holes 18*b* and 18*a* decreased. In catheter Concept E, the septal hole diameters of septal holes 17*d*, 17*c*, 17*b*, and 17*a* were changed to 0.5, 0.75, 1, and 1.5 mm, respectively. In Concept E, fluid velocity decreases were observed at proximal most wall holes 18*d* (41%) and 18*c* (16%), but a substantial increase in fluid velocity was observed at wall hole 18*a* (37%). As noted above, during drainage, wall holes 18 can become clogged. Wall holes towards the distal end portion 13 of the catheter can be more susceptible to clogging than wall holes 18 towards the proximal end portion 12 of the catheter. Accordingly, septal hole diameters can be specified to produce an increased fluid velocity towards the distal end portion 13 of the catheter. Increasing fluid velocity at the septal holes 17 and/or of the wall holes 18 can help dislodge clogged material and maintain catheter patency.

TABLE 4

Concept Catheter Structures D and E with changes in septal hole diameters. Comparison of wall hole flow velocities in Concepts D and E with Baseline Catheter (Concept A) having equal sized septal holes.

| Catheter Design Concept | Wall Hole 18d (cm/s) | Wall Hole 18c (cm/s) | Wall Hole 18b (cm/s) | Wall Hole 18a (cm/s) |
|---|---|---|---|---|
| Concept A: Baseline Catheter | 0.94 | 1.09 | 1.29 | 1.42 |
| Concept D: increased Septal Hole Diameter (1-3 mm) | 0.95 | 1.1 | 1.25 | 1.36 |
| Concept E: Increased Septal Hole Diameter (0.5-1 mm) | 0.55 | 0.92 | 1.31 | 1.94 |

Iterative CFD Comparative Analysis: Changing Drain and Flush Lumen Volumetric Properties (Concepts F and G)

Regarding FIG. 18 and corresponding Table 5, in catheter Concepts F and G a CFD comparative analysis of structures incorporating different volumetric proportions between the waste lumen 15 (i.e., drain lumen) and flush lumen 16 was performed. In the 60:40 drain-to-flush proportion structure (Concept F), there were minimal differences in fluid velocity across all wall holes. Only wall hole 18*b* fluctuated by 0.01 cm/s. However, the 80:20 drain-to-flush proportion structure (Concept G) showed larger effects on the wall hole fluid velocity. Compared to the baseline catheter, wall holes 18*d* and 18*c* in Concept G decreased by 21% and 7%, respectively, while wall holes 18*b* and 18*a* increased by 2% and 13%, respectively.

TABLE 5

Concept Catheter Structures F and G wall hole flow velocities compared to Baseline Catheter (Concept A) with 50:50 Drain:Flush lumen proportions: Changes in septal hole diameter in Concepts F-G compared to the baseline catheter Concept A with equal sized drain and flush lumens.

| Catheter Design Concept | Wall Hole 18d (cm/s) | Wall Hole 18c (cm/s) | Wall Hole 18b (cm/s) | Wall Hole 18a (cm/s) |
|---|---|---|---|---|
| Concept A: Baseline Catheter | 0.94 | 1.09 | 1.29 | 1.42 |
| Concept F: 60:40 Drain:Flush Lumen Proportions | 0.94 | 1.09 | 1.28 | 1.42 |
| Concept G: 80:20 Drain:Flush Lumen Proportions | 0.74 | 1.01 | 1.32 | 1.6 |

Iterative CFD Comparative Analysis: Adding Outward Flush Hole (Concept H) Reduces Wall Hole Flow Velocities Regarding FIG. 19 and corresponding Table 6, a CFD comparative analysis of Catheter Concept H including both septal holes 17*a*-17*d* and outward flush holes 22*a*-22*d* was performed using flushing only. It was hypothesized that including outward flush holes 22_a_-22_d_ would allow for more direct irrigation of an abscess cavity. However, CFD analysis of Concept H having outward flush holes 22_a_-22_d_ demonstrates a substantial decrease in flush fluid flow velocity across wall holes 18_a_-18_d_. In particular, there was over 40% reduction in the fluid flow velocity at wall holes 18_a_-18_d_ in Concept H when compared to Concept A having septal flush holes (but no outward flush holes 22_a_-22_d_). Thus, including inward and outward flush holes can result in lower fluid velocity through wall holes 18_a_-18_d_ and an increased likelihood of obstructive debris at drainage wall holes 18_a_-18_d_.

TABLE 6

Concept Catheter Structure H with outward flush holes compared to Baseline Catheter (Concept A): Adding outward flush holes 22a-22d reduced fluid flow at the drainage wall holes 18a-18d.

| Catheter Design Concept | Wall Hole 18d (cm/s) | Wall Hole 18c (cm/s) | Wall Hole 18b (cm/s) | Wall Hole 18a (cm/s) |
|---|---|---|---|---|
| Concept A: Baseline Catheter | 0.38 | 0.54 | 0.72 | 0.78 |
| Concept H: Septal and Outward Flush Holes | 0.12 | 0.24 | 0.38 | 0.48 |

Regarding FIG. 20 and corresponding Table 7, a CFD comparative analysis of Catheter Concept I including a distal end hole was performed. It was hypothesized that the fluid flow from the distal end hole was negligible. CFD analysis of Concept I having a distal end hole found minimal, proportional decreases in fluid velocity across wall holes 18_a_-18_d_ in a comparison between the baseline catheter Concept A and Concept I have a distal end hole. Thus, the impact of a distal end hole of wall hole fluid velocities and the corresponding CFD analysis can be considered negligible.

TABLE 7

Concept Catheter Structure I with distal end hole has negligible impact on wall hole flow velocities.

| Catheter Design Concept | Wall Hole 18d (cm/s) | Wall Hole 18c (cm/s) | Wall Hole 18b (cm/s) | Wall Hole 18a (cm/s) |
|---|---|---|---|---|
| Concept A: Baseline Catheter Distal End Hole Excluded | 0.94 | 1.09 | 1.28 | 1.45 |
| Concept I: Distal End Hole Included | 0.91 | 1.03 | 1.2 | 1.35 |

Discussion of CFD Results

Using both parametric CAD modeling and CFD software, catheter structural concepts can be rapidly analyzed and iterated using physics-based simulations. Various concepts can be tested with the goal to maximize fluid velocities evenly across all wall holes 18_a_-18_d_ and CFD result comparisons can be performed.

By including a brief suction pump reversal during the flushing action, this structural change can lead to sizable fluid velocity increases across all wall holes in comparison to the flush only action. Although wall hole 18_d_ showed the largest velocity increase (147%), all other wall hole fluid velocities nearly doubled, when compared to the flush only condition. The flush with simultaneous suction pump reversal condition can be nearly as effective as a hypothetical saline flush at 2 times the initial velocity, with minimal fluid velocity loss (less than 17%) due to fluid interferences at lumen junctions. Thus, this concept can be adopted into the final structure and applied to all ensuring CFD simulations.

It was observed that many catheter internal structural modifications could improve overall fluid flow, but only if parameters were crafted carefully. In suboptimal designs such as shifting the holes proximally by 6.5 mm or increasing septal hole diameters to 0.5-1.5 mm, the resulting fluid velocity at the wall holes would decrease in some wall holes, but then increase in the remaining wall holes. These structural changes can be diverting only fluid flow across wall holes, without reducing fluid interferences, substantially. In contrast, shifting the septal holes by 1 mm improved the velocities across all wall holes. These structural changes redirected the fluid flow along more optimal pathways so that fluid interactions were minimized. Enlarging the septal hole along the septum mainly increased the fluid velocity in the most-distal holes, while shifting the septal holes proximally mainly improved fluid velocity at the most proximal wall holes. Furthermore, Catheter Concept G with the 80:20 drain-to-flush lumen proportion confers the benefit of drainage during nominal abscess waste removal operations. Flushing strength would be marginally affected as wall hole 18_d_ fluid velocity decreased by 0.20 m/s (21%) and fluid velocity gains were observed in wall hole 18_a_ by 0.18 m/s (13%). The CFD analysis indicates that internal catheter structural changes can lead to noticeable fluid dynamics changes in a dual-lumen catheter during flushing.

Caveats and limitations to CFD analysis includes assuming fluids are homogenous, whereas in a clinical use case, the waste lumen may contain material that is more viscous. Furthermore, the transient fluid interactions at the startup of the were largely ignored in this steady state analysis. It was theorized that the fast fluid flow velocities would achieve steady state flow quickly inside the relatively small volume of the catheter. Limitations with the steady state CFD analysis were supplemented with physical benchtop testing. Although these limitations can affect the fidelity of the CFD results, the results still provided reasonable and practical knowledge during the virtual, rapid prototyping phase without the need to build numerous costly prototypes.

Additional operational states and structural parameters can further improve flushing. For example, the strength of flush and/or suction pumps can be adjusted to manipulate fluid velocity profiles. During the CFD analysis, only the flushing phase of the catheter was analyzed. However, the catheter can perform several different actions such as performing waste lumen drainage while a flush action is simultaneously occurring to cleanse the waste lumen.

Methods for Percutaneous Drainage

FIG. 21 illustrates an example method 1000 for percutaneous drainage of a drainage site. The method 1000 can begin at step 1100, where the method includes inserting a catheter into the drainage site. The catheter including a catheter wall extending from a proximal end portion of the catheter to a distal end portion of the catheter, the distal end portion of the catheter configured for placement within the drainage site; a septum disposed within the catheter wall and extending from a proximal end portion of the catheter to a distal end portion of the catheter; a drain lumen defined by a first portion of the catheter wall and the septum, and extending from the proximal end portion of the catheter to the distal end portion of the catheter; and a flush lumen defined by a second portion of the catheter wall and the septum, and extending from the proximal end portion of the catheter to the distal end portion of the catheter, wherein the flush lumen is separated from the drain lumen by the septum.

The septum has at least one septal hole disposed therein proximate to the distal end portion of the catheter such that the drain lumen and the flush lumen are in communication via the at least one septal hole; and wherein the catheter wall has at least one wall hole disposed therein proximate to the distal end portion of the catheter such that the drain lumen is in communication with the drainage site when the distal end portion is placed within the drainage site. At step 1200 the method can include withdrawing fluid from the drainage site via the drain lumen. At step 1300 the method can include identifying an occlusion in the drain lumen. At step 1400 the method can include flushing a flush fluid through the flush lumen and into the drain lumen via the at least one septal hole and thereby removing the occlusion. In accordance with the disclosed subject matter, the method can repeat one or more steps of the method of FIG. 21, where appropriate. Although this disclosure describes and illustrates particular steps of the method of FIG. 21 as occurring in a particular order, this disclosure contemplates any suitable steps of the method of FIG. 21 occurring in any suitable order. Moreover, although this disclosure describes and illustrates an example method for percutaneous drainage of a drainage site including the particular steps of the method of FIG. 21, this disclosure contemplates any suitable method for percutaneous drainage of a drainage site including any suitable steps, which can include all, some, or none of the steps of the method of FIG. 21, where appropriate. Furthermore, although this disclosure describes and illustrates particular components, devices, or systems carrying out particular steps of the method of FIG. 21, this disclosure contemplates any suitable combination of any suitable components, devices, or systems carrying out any suitable steps of the method of FIG. 21.

Where system 100 is used for percutaneous thoracostomy, the sensor/microcontroller system can be further programmed to detect the presence, persistence, and/or resolution of pneumothorax, air leak, and/or bronchopleural fistula. Where system 100 is used for percutaneous chemical ablation and/or sclerosis of cystic lesions, recurrent fluid collections (such as lymphoceles and other disorders of the lymphatic system), and/or hollow viscera (such as gallbladder in candidates deemed unsuitable for cholecystectomy), the system can monitor volume of injected sclerosant/polymer glue, dwell time, irrigation, simultaneous or delayed aspiration, repeated cycles. In such use, the catheter 10 can be provided with side holes along both of its outer walls 11 and no septal holes 17. Where the system is used for percutaneous esophagostomy gastrostomy, gastrojejunostomy, jejunostomy, and/or cecostomy (i.e., the alimentary/digestive tract), the system can include programmable tube feeding setting for patient-specific nutritional needs, and tube flushing settings for maintenance of luminal patency.

Enteral Feeding

Regarding FIG. 22, system 100C is configured for use with enteral (e.g., gastrostomy, gastrojejunostomy, jejunostomy) feeding catheters (e.g., enteral tube 72). For example, indwelling percutaneous gastrostomy catheter 71 can feed the stomach with liquid nutrition formula from container 73 via peristaltic pump 102*a* instillation. A pressure sensor 75 installed along the tubing between container 73 and indwelling percutaneous gastrostomy catheter 71 enables detection of luminal occlusion due to feed concretions or other particulate matter. In the event of occlusion, control unit 60 activates a second peristaltic pump 102*b* attached to container 74 filled with sterile water or saline, thereby enabling powered flushing and restoration of tube patency. Flushing can also be regularly scheduled with preset volume and pressure for tube maintenance. Optional syringe pump 76 allows for administration of prescribed medications per the enteral tube 72.

While the disclosed subject matter is described herein in terms of certain preferred embodiments for purpose of illustration and not limitation, those skilled in the art will recognize that various modifications and improvements can be made to the disclosed subject matter without departing from the scope thereof. Moreover, although individual features of one embodiment of the disclosed subject matter can be discussed herein or shown in the drawings of one embodiment and not in other embodiments, it should be readily apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A system for percutaneous drainage of a drainage site, comprising:

a catheter having a catheter wall extending from a proximal end portion of the catheter to a distal end portion of the catheter, the distal end portion of the catheter configured for placement within the drainage site, a septum disposed within the catheter wall and extending from a proximal end portion of the catheter to a distal end portion of the catheter, wherein the distal end portion includes a distal tip of the catheter, the septum extending completely to the distal tip of the catheter;

a drain lumen defined by a first portion of the catheter wall and the septum, and extending from the proximal end portion of the catheter to the distal end portion of the catheter, and a flush lumen defined by a second portion of the catheter wall and the septum, and extending from the proximal end portion of the catheter to the distal end portion of the catheter, wherein the flush lumen is separated from the drain lumen by the septum;

a drain tube having a first end portion coupled to the drain lumen at the proximal end portion of the catheter, and a second end portion coupled to a waste collection container;

a first pump coupled to the drain tube between the first end portion of the drain tube and the second end portion of the drain tube;

a flush tube having a first end portion coupled to the flush lumen at the proximal end portion of the catheter, and a second end portion coupled to a flush material container having a flush material disposed therein;

a second pump coupled to the flush tube between the first end portion of the flush tube and the second end portion of the flush tube; and a controller coupled to the first pump and the second pump for controlling the first pump and the second pump;

wherein the septum has a plurality of septal holes in the septum along a longitudinal axis of the catheter, the plurality of septal holes disposed proximate to the distal end portion of the catheter such that the drain lumen and the flush lumen are in communication via the plurality of septal holes;

wherein the catheter wall has a plurality of wall holes in the catheter wall along the longitudinal axis of the catheter, the plurality of wall holes disposed proximate to the distal end portion of the catheter such that the drain lumen is in communication with the drainage site when the distal end portion is placed within the drainage site;

wherein each of the wall holes of the plurality of wall holes has a corresponding septal hole of the plurality of septal holes; and wherein each wall hole is aligned with the corresponding septal hole such that each wall hole is positioned between 1 mm and 6.5 mm of the corresponding septal hole along the longitudinal axis.

2. The system of claim 1, wherein a volume of the drain lumen is equal to a volume of the flush lumen.

3. The system of claim 1, wherein a volume of the drain lumen is greater than the volume of the flush lumen.

4. The catheter of claim 1, wherein the plurality of septal holes comprises a distal hole having a first diameter and a proximal hole having a second diameter, the second diameter being different than the first diameter.

5. The system of claim 4, wherein the second diameter is smaller than the first diameter.

6. The system of claim 1, further comprising a pressure sensor coupled to the drain tube and the controller.

7. The system of claim 1, further comprising a housing having the first pump, the second pump, and the controller disposed therein.

8. The system of claim 1, further comprising an injection port coupled to the flush tube.

9. The system of claim 8, further comprising a syringe coupled to the injection port by a third tube.

10. The system of claim 8, further comprising a third pump coupled to the injection port by a third tube.

11. A catheter for percutaneous drainage of a drainage site, comprising:

a catheter wall extending from a proximal end portion of the catheter to a distal end portion of the catheter, the distal end portion of the catheter configured for placement within the drainage site;

a septum disposed within the catheter wall and extending from the proximal end portion of the catheter to the distal end portion of the catheter;

wherein the distal end portion includes a distal tip of the catheter, the septum extending completely to the distal tip of the catheter;

a drain lumen defined by a first portion of the catheter wall and the septum, and extending from the proximal end portion of the catheter to the distal end portion of the catheter; and a flush lumen defined by a second portion of the catheter wall and the septum, and extending from the proximal end portion of the catheter to the distal end portion of the catheter, wherein the flush lumen is separated from the drain lumen by the septum;

wherein the septum has at least one septal hole disposed therein proximate to the distal end portion of the catheter such that the drain lumen and the flush lumen are in communication via the at least one septal hole;

wherein the catheter wall has at least one wall hole disposed therein proximate to the distal end portion of the catheter such that the drain lumen is in communication with the drainage site when the distal end portion is placed within the drainage site;

wherein each wall hole has a corresponding septal hole; and wherein each wall hole is aligned with each corresponding septal hole such that each wall hole is positioned between 1 mm and 6.5 mm of the corresponding septal hole along the longitudinal axis.

12. The catheter of claim 11, wherein a volume of the drain lumen is equal to a volume of the flush lumen.

13. The catheter of claim 11, wherein a volume of the drain lumen is greater than the volume of the flush lumen.

14. The catheter of claim 11, wherein the at least one septal hole comprises a plurality of septal holes.

15. The catheter of claim 11, wherein the at least one septal hole comprises a distal hole having a first diameter and a proximal hole having a second diameter, the second diameter being different than the first diameter.

16. The catheter of claim 15, wherein the second diameter is smaller than the first diameter.

17. The catheter of claim 11, wherein the at least one septal hole and the at least one wall hole are offset.

18. A method of percutaneous drainage of a drainage site, comprising:

inserting a catheter into the drainage site, the catheter including a catheter wall extending from a proximal end portion of the catheter to a distal end portion of the catheter, the distal end portion of the catheter configured for placement within the drainage site;

a septum disposed within the catheter wall and extending from a proximal end portion of the catheter to a distal end portion of the catheter;

a drain lumen defined by a first portion of the catheter wall and the septum, and extending from the proximal end portion of the catheter to the distal end portion of the catheter; and a flush lumen defined by a second portion of the catheter wall and the septum, and extending from the proximal end portion of the catheter to the distal end portion of the catheter, wherein the flush lumen is separated from the drain lumen by the septum;

wherein the septum has at least one septal hole disposed therein proximate to the distal end portion of the catheter such that the drain lumen and the flush lumen are in communication via the at least one septal hole;

wherein the catheter wall has at least one wall hole disposed therein proximate to the distal end portion of the catheter such that the drain lumen is in communication with the drainage site when the distal end portion is placed within the drainage site;

wherein each of the wall holes has a corresponding septal hole; and wherein each wall hole is aligned with the corresponding septal hole such that each wall hole is positioned between 1 mm and 6.5 mm of the corresponding septal hole along the longitudinal axis;

withdrawing fluid from the drainage site via the drain lumen;

identifying an occlusion in the drain lumen and;

flushing a flush fluid through the flush lumen and into the drain lumen via the at least one septal hole and thereby removing the occlusion.

19. The method of claim 18, further comprising pausing withdrawing fluid from the drainage site via the drain lumen.

20. The method of claim 19, wherein pausing further comprises reversing a direction of fluid flow in the drain lumen.

21. The method of claim 19, further comprising resuming withdrawing fluid from the drainage site vide the drain lumen.

22. The method of claim 19, further comprising monitoring a rate of fluid withdrawal from the drainage site.

23. The method of claim 22, further comprising monitoring a rate of change of the rate of fluid withdrawal from the drainage site.

24. The method of claim 23, where identifying an occlusion in the drain lumen is based at least in part on one or more of the rate of fluid withdrawal from the drainage site and the rate of change of the rate of fluid withdrawal from the drainage site.

25. The method of claim 19, further comprising monitoring a pressure in the waste lumen.

26. The method of claim 25, further comprising monitoring a rate of change of the pressure in the waste lumen.

27. The method of claim 26, wherein identifying an occlusion in the drain lumen is based at least in part on one or more of the pressure in the waste lumen and a rate of change of the pressure in the waste lumen.

28. A system for percutaneous drainage of a drainage site, comprising:

a catheter having a catheter wall extending from a proximal end portion of the catheter to a distal end portion of the catheter, the distal end portion of the catheter configured for placement within the drainage site, a septum disposed within the catheter wall and extending from a proximal end portion of the catheter to a distal end portion of the catheter, wherein the distal end portion includes a distal tip of the catheter, the septum extending completely to the distal tip of the catheter;

a drain lumen defined by a first portion of the catheter wall and the septum, and extending from the proximal end portion of the catheter to the distal end portion of the catheter, and a flush lumen defined by a second portion of the catheter wall and the septum, and extending from the proximal end portion of the catheter to the distal end portion of the catheter, wherein the flush lumen is separated from the drain lumen by the septum, wherein the septum has a plurality of septal holes in the septum along a longitudinal axis of the catheter;

a drain tube having a first end portion coupled to the drain lumen at the proximal end portion of the catheter, and a second end portion coupled to a waste collection container;

a first pump coupled to the drain tube between the first end portion of the drain tube and the second end portion of the drain tube;

a flush tube having a first end portion coupled to the flush lumen at the proximal end portion of the catheter, and a second end portion coupled to a flush material container having a flush material disposed therein;

a second pump coupled to the flush tube between the first end portion of the flush tube and the second end portion of the flush tube; and a controller coupled to the first pump and the second pump for controlling the first pump and the second pump;

wherein the first portion of the catheter wall has at least a first wall hole disposed therein proximate to the distal end portion of the catheter such that the drain lumen is in communication with the drainage site when the distal end portion of the catheter is placed within the drainage site;

wherein the second portion of the catheter wall has at least a second wall hole disposed therein proximate to the distal end portion of the catheter such that the flush lumen is in communication with the drainage site when the distal end portion of the catheter is placed within the drainage site;

wherein each wall hole has a corresponding septal hole of the plurality of septal holes; and wherein each wall hole is aligned with the corresponding septal hole such that each wall hole is positioned between 1 mm and 6.5 mm of the corresponding septal hole along the longitudinal axis.

29. The catheter of claim 1, wherein the drain lumen includes a hole at the distal tip of the catheter for delivery of a guidewire.

30. The catheter of claim 11, wherein the drain lumen includes a hole at the distal tip of the catheter for delivery of a guidewire.

31. The catheter of claim 28, wherein the drain lumen includes a hole at the distal tip of the catheter for delivery of a guidewire.

* * * * *